US011647962B2

(12) United States Patent
Kremen et al.

(10) Patent No.: US 11,647,962 B2
(45) Date of Patent: May 16, 2023

(54) SYSTEM AND METHOD FOR CLASSIFYING AND MODULATING BRAIN BEHAVIORAL STATES

(71) Applicant: Mayo Foundation for Medical Education and Research, Rochester, MN (US)

(72) Inventors: Vaclav Kremen, Rochester, MN (US); Brent M. Berry, Rochester, MN (US); Benjamin I. Brinkmann, Byron, MN (US); Squire M. Stead, Rochester, MN (US); Gregory A. Worrell, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 344 days.

(21) Appl. No.: 16/960,679

(22) PCT Filed: Jan. 8, 2019

(86) PCT No.: PCT/US2019/012740
§ 371 (c)(1),
(2) Date: Jul. 8, 2020

(87) PCT Pub. No.: WO2019/136462
PCT Pub. Date: Jul. 11, 2019

(65) Prior Publication Data
US 2020/0337645 A1 Oct. 29, 2020

Related U.S. Application Data

(60) Provisional application No. 62/614,766, filed on Jan. 8, 2018.

(51) Int. Cl.
*A61B 5/00* (2006.01)
*A61B 5/11* (2006.01)
(Continued)

(52) U.S. Cl.
CPC .......... *A61B 5/7264* (2013.01); *A61B 5/0006* (2013.01); *A61B 5/1118* (2013.01);
(Continued)

(58) Field of Classification Search
CPC ..... A61B 5/0006; A61B 5/1118; A61B 5/165; A61B 5/24; A61B 5/316; A61B 5/374;
(Continued)

(56) References Cited

U.S. PATENT DOCUMENTS

2003/0074033 A1* 4/2003 Pless ............... G16H 40/60
607/48
2009/0192556 A1 7/2009 Wu et al.
(Continued)

OTHER PUBLICATIONS

ElMessidi et al., "Accurate Automatic Identification of Slow Wave Sleep sing a Single Electro-oculogram Channel", Feb. 17-20, 2014, Middle East Conference on Biomedical Engineering (MECBME).
(Continued)

*Primary Examiner* — Michael W Kahelin
*Assistant Examiner* — Vynn V Huh
(74) *Attorney, Agent, or Firm* — Daniel J. Chalker; Edwin S. Flores; Chalker Flores, LLP

(57) ABSTRACT

A behavioral state of a brain is classified by automatically selecting one or more sensors based on the signals received from each sensor and one or more selection criteria using one or more processors, calculating at least one measured value from the signal(s) of the selected sensor(s), classifying the behavioral state as: (a) an awake state whenever the measured value(s) for the selected sensor(s) is lower than a first threshold value, (b) a sleep state (N2) whenever the measured value(s) for the selected sensor(s) is equal to or greater than the first threshold value and the measured value(s) is not greater than a second threshold value, or (c) a slow wave sleep state (N3) whenever the measured value(s) from the selected sensor(s) is greater than the first
(Continued)

threshold value and the measured value(s) is greater than the second threshold value, and providing a notification of the classified behavioral state.

19 Claims, 9 Drawing Sheets

(51) Int. Cl.
*A61B 5/16* (2006.01)
*A61B 5/24* (2021.01)
*A61B 5/316* (2021.01)
*A61B 5/374* (2021.01)
*A61B 5/389* (2021.01)
*A61N 1/36* (2006.01)
*A61N 1/04* (2006.01)
*A61N 1/05* (2006.01)

(52) U.S. Cl.
CPC ............... *A61B 5/165* (2013.01); *A61B 5/24* (2021.01); *A61B 5/316* (2021.01); *A61B 5/374* (2021.01); *A61B 5/389* (2021.01); *A61B 5/4094* (2013.01); *A61B 5/4809* (2013.01); *A61B 5/4812* (2013.01); *A61B 5/7267* (2013.01); *A61B 5/746* (2013.01); *A61B 5/7475* (2013.01); *A61B 5/6868* (2013.01); *A61N 1/36135* (2013.01)

(58) Field of Classification Search
CPC ..... A61B 5/389; A61B 5/4094; A61B 5/4809; A61B 5/4812; A61B 5/4836; A61B 5/6868; A61B 5/7264; A61B 5/7267; A61B 5/746; A61B 5/7475; A61N 1/36135
See application file for complete search history.

(56) References Cited

U.S. PATENT DOCUMENTS

| | | |
|---|---|---|
| 2011/0257517 A1 | 10/2011 | Guttag et al. |
| 2011/0301487 A1 | 12/2011 | Abeyratne et al. |
| 2012/0277618 A1 | 11/2012 | Giftakis et al. |
| 2014/0107520 A1* | 4/2014 | Hang ................... A61B 5/4812 600/544 |
| 2014/0121554 A1 | 5/2014 | Sarma et al. |
| 2016/0151012 A1* | 6/2016 | Bozkurt ................ A61B 5/688 600/323 |
| 2017/0311878 A1 | 11/2017 | Wu et al. |
| 2018/0092600 A1* | 4/2018 | Simons ................ A61B 5/4812 |

OTHER PUBLICATIONS

Kremen et al., "Behavioral State Classification in Epileptic Brain using Intracranial Electrophysiology", J Neural Eng. Apr. 2017; 14(2): 026001, Neural Eng. Author manuscript.

Patrick et al., "An Algorithm for Automatic Detection of Drowsiness for Use in Wearable EEG Systems", Aug. 2016, International Conference of the IEEE Engineering in Medicine and Biology Society.

Radha et al., "Comparison of Feature and Classifier Algorithms for Online Automatic Sleep Staging Based on a Single EEG Signal", 2014 36th Annual International Conference of the IEEE Engineering in Medicine and Biology Society.

Kremen, V. etal., "Behavioral State Classification in Epileptic Brain using Intracranial Electrophysiology", J. Neural Eng. Apr. 2017, 14(2): 026001, doi: 10.1088/1741-2552/aa5688.

* cited by examiner

SYSTEM AND METHOD FOR CLASSIFYING AND MODULATING BRAIN BEHAVIORAL STATES

CROSS-REFERENCE TO RELATED APPLICATIONS

This application claims priority to and is a National Stage of International Application No. PCT/US2019/012740 filed on Jan. 8, 2019, which claims priority to U.S. Provisional Patent Application No. 62/614,766 filed on Jan. 8, 2018, the entire contents of each of which is incorporated by reference herein.

TECHNICAL FIELD OF THE INVENTION

The present invention relates in general to tracking human brain activity, and more particularly, to a system and method for classifying and modulating brain behavioral states.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with human brain behavioral states that include stages of wakefulness and sleep.

An automated behavioral state classification can be beneficial for the next generation of implantable brain stimulation devices, and would enable for example behavioral-state-dependent seizure prediction (Cook et al. 2013; Brinkmann et al. 2015; Brinkmann et al. 2016; Ramgopal et al. 2014), and electrical stimulation therapies (Bower et al. 2015; Lundstrom, B.N et al. 2016; Salanova et al. 2015) in devices for treatment of drug resistant epilepsy, cognitive disorders, and sleep disorders. Additional applications include brain stimulation for cognitive and mood enhancement where it may be beneficial to deliver electrical stimulation in particular brain states, or to adjust the stimulation therapy depending on brain state to improve cognition or mood. Human scalp EEG is the cornerstone of sleep scoring (Rechtschaffen and Kales 1968) and has been routinely used in clinical practice to score behavioral states into awake (AW), drowsiness (N1), sleep (N2), and deep sleep (N3). Relatively little investigation has been done in the feasibility of sleep staging using intracranial EEG (iEEG) recordings rather than scalp EEG (Kelsey et al. 2012) (Pahwa et al. 2015) (Zempel et al. 2012). Implanted brain stimulation devices have intracranial electrodes for stimulation and recording, and therefore brain state classification and tracking using iEEG is proposed here as a way to track brain activity. Compared to others, Kremen et al. (2017) have directly investigated different brain structures and the impact of tissue pathology, i.e. seizure onset zone (SOZ) or non-seizure onset zone (NON-SOZ) on differentiation of awake (AW) and slow-wave sleep (N3), and described classifiers using iEEG signals from one intracranial electrode to distinguish between AW and N3. Yet, this approach was supervised and a priori knowledge of gold standard from scalp EEG recording and iEEG training data was essential.

SUMMARY OF THE INVENTION

The present invention provides technology for automated wake (W), rapid eye movement (REM), and non-REM and non-REM categories (NREM: N1, N2, N3 (including microstates)) sleep classification using human EEG data recorded from locations other than scalp, including subscalp, epidural and intracranial EEG. This technology provides a powerful tool for implementation in next-generation implantable devices that can measure, track and control brain behavioral states. An efficient, automated method for behavioral state classification is needed for next generation implantable devices that have limited computational power, memory, and electrode numbers. Applications include quantifying patient sleep patterns and delivering behavioral state dependent modulation with electrical stimulation therapies for neurological diseases, and optimizing brain states for neurologic and psychiatric health.

In one embodiment, a system for classifying a brain behavioral state comprises a sensor and/or electrode interface, a user interface, a data storage or memory, and one or more processors communicably coupled to the sensor and/or electrode interface, the user interface and data storage or memory. The one or more processors: receive a signal from each of a plurality of sensors via the sensor and/or electrode interface, automatically select one or more of the sensors based on the signals received from each sensor and one or more selection criteria, calculate at least one measured value from the signal(s) of the selected sensor(s), classify the behavioral state as: (a) an awake state whenever the measured value(s) for the selected sensor(s) is lower than a first threshold value, (b) a sleep state (N1 or N2) whenever the measured value(s) for the selected sensor(s) is equal to or greater than the first threshold value and the measured value(s) is not greater than a second threshold value, or (c) a slow wave sleep state (N3) whenever the measured value(s) from the selected sensor(s) is greater than the first threshold value and the measured value(s) is greater than the second threshold value, and provide a notification of the classified behavioral state to the user interface. Other aspects of the invention are described in the detailed description and figures.

In another embodiment, a computerized method of classifying a behavioral state of a brain comprises providing a plurality of sensors configured to detect an electrical activity of the brain, and providing one or more processors communicably coupled to a user interface and the plurality of sensors. A signal is received from each of the plurality of sensors, one or more of the sensors are automatically selected based on the signals received from each sensor and one or more selection criteria using the one or more processors, and at least one measured value is calculated from the signal(s) of the selected sensor(s) using the one or more processors. The behavioral state is classified as: (a) an awake state whenever the measured value(s) for the selected sensor(s) is lower than a first threshold value, (b) a sleep state (N1 or N2) whenever the measured value(s) for the selected sensor(s) is equal to or greater than the first threshold value and the measured value(s) is not greater than a second threshold value, or (c) a slow wave sleep state (N3) whenever the measured value(s) from the selected sensor(s) is greater than the first threshold value and the measured value(s) is greater than the second threshold value. The signals can also be optimized for classifying rapid eye movement (REM) sleep and a multitude of sleep microstates (NJ$_i$ where J=1, 2, 3 denotes the classically defined sleep states (N1, N2, N3) and i=1, 2, 3, . . . , m denotes the microstates within each of the classically defined sleep states (N1, N2, N3). Thereafter, a notification of the classified behavioral state is provided to the user interface. The interface algorithm can adjust electrical stimulation based on pre-determined optimal brain state dependent stimulation protocols. Other aspects of the invention are described in the detailed description and figures. Moreover, the method can be implemented using a non-transitory computer readable medium that when executed causes the one or more processors to perform the method.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
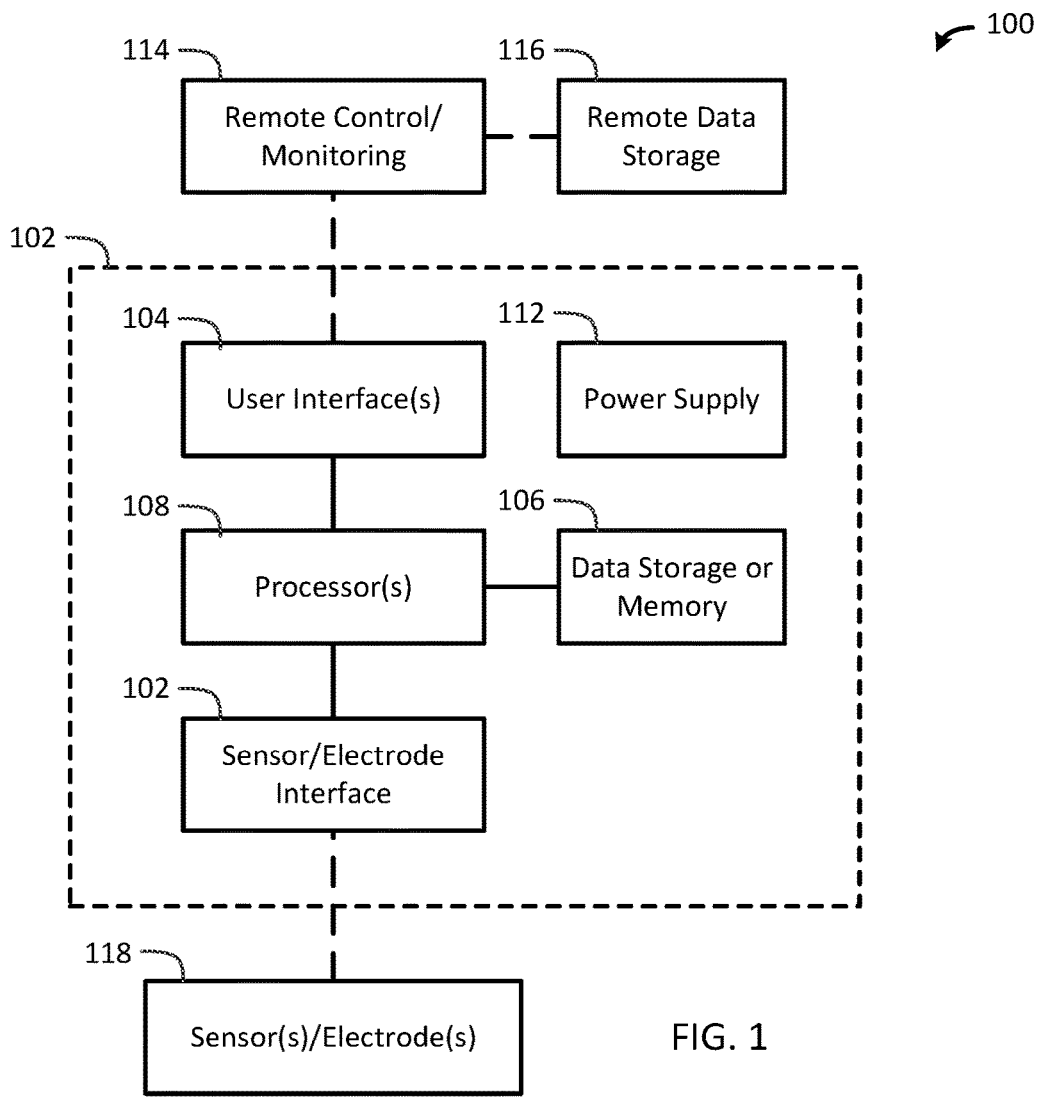
FIG. 1 illustrates a block diagram of a system in accordance with one embodiment of the present invention.
Figure 2:
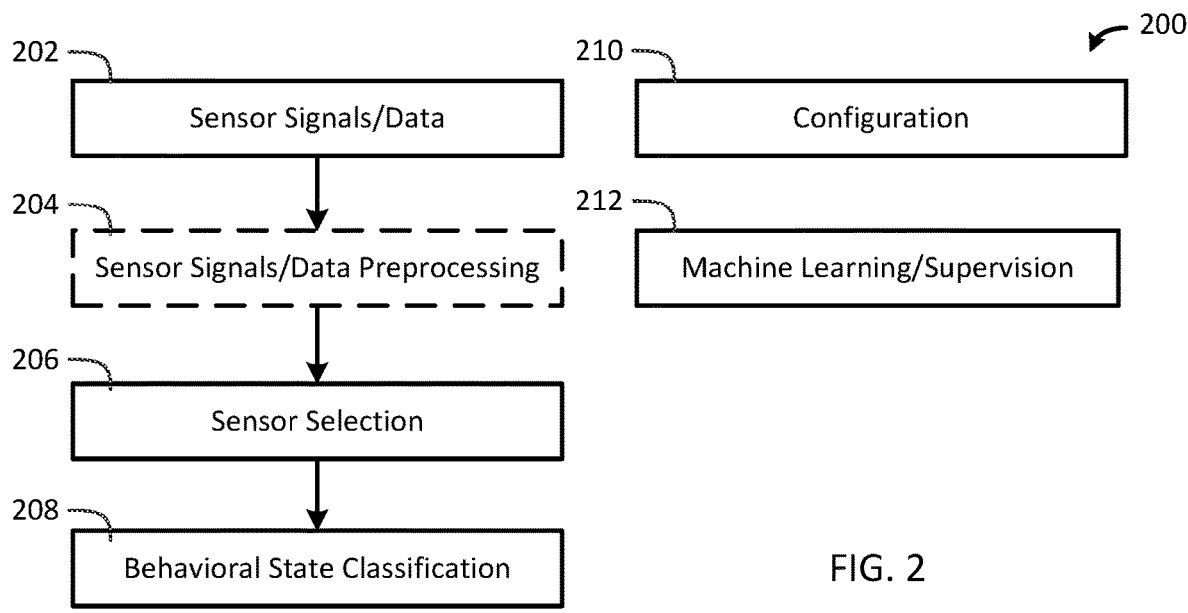
FIG. 2 illustrates a block diagram of various modules or functions in accordance with one embodiment of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

A role of an automated behavioral state classification can be beneficial for a next generation of implantable brain stimulation devices. Here, a fully automated unsupervised method to differentiate between awake (AW), sleep (N2), and slow wave sleep (N3) classification using intracranial EEG (iEEG) is described. During testing, data from eight patients undergoing evaluation for epilepsy surgery (age 40±11, 3 women) who underwent intracranial depth electrode implantation for iEEG monitoring were included. Spectral power features (0.1-235 Hz) spanning several frequency bands from a single electrode were used to classify behavioral states of patients into AW, N2, and N3. Overall, classification accuracy of 94% with 94% sensitivity and 93% specificity across eight subjects using multiple spectral power features from a single electrode was achieved. Classification performance of N3 stage was significantly better (96%, sensitivity 97%, specificity 94%) than of N2 sleep phase (88%, sensitivity 78%, specificity 97%). As a result, automated unsupervised classification of behavior states based on iEEG data can be useful for future implantable devices for brain monitoring and stimulation. The classification of N1 and REM using a similar approach is feasible, but may require multiple electrode/sensor signals. Devices with limited computational power, memory, and number of electrodes can benefit from minimalized and robust methods such as the one described herein. The present invention can be used in applications quantifying patient sleep patterns and behavioral state dependent seizure detection and prediction, and electrical stimulation therapies.

The potential applications of automated behavioral state classification in next generation implantable neuromodulation devices span many neurological and psychiatric diseases, and diseases that have various patterns following sleep-wake cycles, including: epilepsy, cognition disorders, movement disorders, sleep disorders, mood & behavioral disorders, neuropathy & pain disorders, spasticity, complex regional pain syndrome, cancer pain, migraine, spinal cord injury, gastric diseases, incontinence, pelvic floor disease and PVD. Accordingly, a system and method for automated brain state classification (Wake, Drowsy, Non-REM {N1, N2, N3 (including microstates)} and REM sleep) using machine learning techniques applied to human EEG recorded from single or multiple scalp, subscalp, epidural, intracranial (subdural & depth) electrodes is described herein.

An immediate application of automated behavioral state classification will be in implantable epilepsy devices. This technology will make possible behavioral-state-dependent seizure prediction (Cook et al. 2013, Ramgopal et al. 2014, Brinkmann et al. 2015 & 2016), and adaptive electrical stimulation therapies guided by brain state (Bergey et al. 2015, Salanova et al. 2015, Lundstrom et al. 2016). Selective stimulation during slow wave sleep to disrupt the consolidation of epileptic engrams (Bower et al. 2015 & 2017), enhance normal memory engrams (McGaugh J L 2000; Leminen et al., 2017; Papalmbros et al., 2017; Santostasi et al., 2016), or disrupt negative memories common in post traumatic stress disorder will be possible with behavioral state classification. In general, sleep and wake states can be modulated using electrical stimulation, and overall sleep-wake dynamics can be fine tuned to meet desired, pre-determined behavioral state patterns by tracking behavioral state and modulating via a control algorithm that adjusts electrical stimulation in different brain regions. For example, sleep quality, characteristics, and patterns can be improved to achieve clinical benefits for patients with sleep disorders. In the substantial and most widely recognized sub-field of neuromodulation and implantable brain devices, Deep Brain Stimulation which were first used in Parkinson's Disease, it has been shown that identification of sleep-wake cycles has consequence for neuromodulation. (Eugster 2016, Sixel-Doring 2011). In addition, medical devices with automated brain state classifiers can provide accurate sleep/wake staging to quantify patient sleep duration and patterns as an objective biomarker of diseases effecting sleep/wake architecture.

The inventors previously demonstrated Wake (AW) and slow-wave sleep (SWS) changes using wide-bandwidth iEEG (0.1-600 Hz) (Worrell 2012) and automated classification of brain behavioral states (wake and slow-wave sleep (N2, N3)) using support vector machines (SVM) classifiers in humans (Kremen 2017). There, spectral characteristics and patterns of brain activity inside and outside of focal seizure-generating brain regions (i.e. SOZ and NON-SOZ) in two distinct human behavioral states (wake and slow-wave sleep) were used to explore the feasibility of automatically differentiating between AW and SWS behavioral states using multiple frequency bands. It was demonstrated that a single iEEG electrode can yield accurate automated classification of AW and SWS evaluated by the gold standard, polysomnography (Iber et al. 2007).

Here, the present invention provides technology for automated wake (W), rapid eye movement (REM), and non-REM (NREM: N1, N2, N3 (including microstates)) sleep classification and sleep microstates using human EEG data recorded from locations other than scalp, including subscalp, epidural and intracranial EEG. The local field potentials have been shown to change discontinuously, exhibiting periods of quasi-stability on the order of 100 ma before abruptly transitioning to another configuration (Lehmann et al., 1987). The periods of quasi-stability have been termed "microstates", and thought to arise from coordinated activity of neural assemblies originating from large areas of the cortex. This technology provides a powerful tool for implementation in next-generation implantable devices. An efficient, automated method for behavioral state classification is needed for next generation implantable devices that have limited computational power, memory, and electrode numbers. Applications include quantifying patient sleep patterns and delivering behavioral state dependent modulation with electrical stimulation therapies.

Now referring to FIG. 1, a block diagram of a system 100 for classifying a behavioral state of a brain in accordance with one embodiment of the present invention is shown. The system 100 can include a sensor and/or electrode interface 102, a user interface 104, a data storage or memory 106, and one or more processors 108 communicably coupled to the sensor and/or electrode interface 102, the user interface 104, and data storage or memory 106. The sensor/electrode interface 102 can be configured to receive and transmit signals to one or more sensors, one or more electrodes, or both. The user interface 104 can be any component or device in which information is transmitted to and/or received from the one or more processors 108. In some embodiments, the user interface 104 can be a connector in which a separate device can be attached, a network interface, a wireless transceiver, a display, a keyboard, a keypad, etc. For example, an application running on a mobile device, such as a phone, electronic tablet or computer, can wirelessly connect to and control/monitor the system 102 via the user interface 104. The system 102 can include a power supply 112 or connection to a power source, such as an AC outlet. The user interface 104 or other component can be used to communicably couple the one or more processors 108 to a remote control/monitoring device 114 and/or remote data storage 116. The power supply 112 may include batteries as a primary power source or a back-up power source. Moreover, the system 102 can be fixed or portable. For example, the system 112 can be provided in a minimized form for home monitoring in which the data/notifications are stored in the data storage or memory 106 for later access by a device connected to the user interface 104, or transmission to a remote control/monitoring device 114 in real time, near-real time, or other time frame.

The one or more processors 108 receive a signal from each of a plurality of sensors 118 via the sensor and/or electrode interface 102. The sensors 118 are configured to detect an electrical activity of the brain. In addition, the sensors 118 can be physically or wirelessly connected to the sensor and/or electrode interface 102. The sensors 118 can be electrodes, such as intracranial electrodes, epidural electrodes, sub-scalp electrodes, scalp electrodes, intracranial or dermal laser sensors, electrodes placed on the body or limbs, interstitial blood glucose or hormone sensors, other types of sensors or electrodes, or a combination thereof. Depending on the embodiment, the sensors 118: (a) can have 10 µm to 10 mm diameter contacts; (b) can record single neurons, assemblies of neurons, or networks of neurons; and/or (c) can record the brain electrical activity over a wide dynamic range DC to 10,000 Hz. (Worrell et al. 2012; Stead et al. 2010; Bower et al. 2015). Note that in some embodiments, the sensors 118 can perform some signal processing and/or analog-to-digital conversion of the signals detected by the sensors 118.

Thereafter, the one or more processors perform various functions or methods that are used to classify the behavioral state of the brain. Non-limiting examples of such functions or methods are shown in FIGS. 2, 3, 7 and 8, and described below. For example, in FIG. 2, the sensor signals/data are received in block 202, the sensor signals/data are preprocessed in block 204 (optional), one or more sensors are selected in block 206, and behavioral state classification is performed in block 208. A user or other device can be used to configure the system 100 in block 210. In addition, machine learning and/or supervision can be used to configure, adjust, fine tune or otherwise operate the system in block 212. In one embodiment, the one or more processors 108: (1) automatically select one or more of the sensors 118 based on the signals received from each sensor 118 and one or more selection criteria, (2) calculate at least one measured value from the signal(s) of the selected sensor(s) 118, (3) classify the behavioral state as: (a) an awake state whenever the measured value(s) for the selected sensor(s) is lower than a first threshold value, (b) a sleep state (N1 or N2) whenever the measured value(s) for the selected sensor(s) is equal to or greater than the first threshold value and the measured value(s) is not greater than a second threshold value, or (c) a slow wave sleep state (N3) whenever the measured value(s) from the selected sensor(s) is greater than the first threshold value and the measured value(s) is greater than the second threshold value, and (4) provide a notification of the classified behavioral state to the user interface 104. In some embodiments, the one or more processors 108 can also classify the brain behavioral state as a drowsy state (N1), a REM state, or a microstate within the drowsy state (N1), the sleep state (N2) or the slow wave sleep state (N3), or a brain state characterized by abundant or excessive pathological activity, or a brain state otherwise identified as representing an elevated probability for occurrence of a seizure. The microstate can be identified by $NJ_i$ where J=1, 2, 3 denotes the classically defined sleep states (N1, N2, N3) and i=1, 2, 3, . . . , m denotes the microstates within each of the classically defined sleep states (N1, N2, N3). Moreover, the one or more processors 108 can store the classified behavioral state in the data storage or memory 106, provide an alert whenever the classified behavioral state is different than a previous classified behavioral state, and/or automatically map one or more spatial and temporal patterns of the classified behavioral state and one or more transitions between the classified behavioral states.

The one or more processors 108 can receive one or more configuration settings via the user interface 104. In some embodiments, the configuration settings can be a manual or automatic sensor selection, a preprocessing algorithm selection, a detection algorithm selection, a feature selection (e.g., power spectral feature, time-domain feature, etc.), a clustering method selection, or a thresholding rule selection. In some embodiments, the receiving, selecting, calculating, classifying and providing steps are performed by the one or more processors 108 using an operational mode comprising: a fully automated and unsupervised mode (e.g., FIG. 4); or a semi-automated mode; or an active learning mode—unsupervised first and supervised by redefining clusters displayed to user (user can reassign each part of the data into different class and retrain); or a supervised mode—fully supervised and trained by expert or trained on known scalp electrophysiology data in parallel with any simultaneous data (e.g. intracranial, epidural, subscalp, EEG, video recording, EMG, actigraphy, etc.); or other desired mode. Note that the clustering method can be selected from any known or future developed clustering method used in machine learning (e.g., K-NN, hierarchical trees, deep learning, neural networks, t-SNE, isomap, Sammon mapping, linear embedding, unsupervised deep embedding, etc.). In some embodiments, other features than described in these examples can be used or inferred unsupervised from the data—e.g., by unsupervised feature learning or deep learning. Depending on the configuration used, the behavioral state can be classified without a gold standard scoring. The one or more processors 108 can also use training signal processing and a machine learning system to identify one or more suitable sensor configurations for an automated or semi-automated classification of the behavioral state. Moreover, the one or more processors 108 select target brain locations for the sensors from one or more of a cortex, hippocampus, thalamus, brain stem, basal ganglia, subthalamic nucleus, globus pallidus or other movement circuitry structures and muscles via EMG or ENG or actigraphy.

In some embodiments, the first threshold value comprises a first Delta power value (e.g., a median relative Delta, etc.) and the second threshold value comprises a second Delta power value (e.g., a $40^{th}$ percentile of the relative Delta, etc.). The one or more processors 108 can pre-process the signals by: detecting an abnormal amplitude distortion in the signals; or detecting a seizure or an abnormal electrophysiological condition using the signals; or detecting a high 60 or 50 Hz line interference in the signals; or other desired process. For example, the one or more processors 108 can select or restrict a number of channels of the sensors 118, or a number of power spectral features of the sensors 118. The one or more selection criteria can be: a power spectral features extraction; or a clustering algorithm (e.g., K-NN, hierarchical trees, deep learning, neural networks, t-SNE, isomap, Sammon mapping, linear embedding, unsupervised deep embedding, etc.); or one or more measures of separability; or other desired criteria. For example, the one or more selection criteria can be a K-NN clustering algorithm with Euclidean distance measure where inter and intra-cluster distance are used as parameters for selection of only one sensor. As will described below, only selecting one sensor can be beneficial and effective.

In some embodiments, the one or more processors 108 can filter the signal(s) into a set of frequency bands for each sensor, calculate an absolute power and a relative power for each of the frequency bands for each sensor, such that automatically selecting the sensor(s) based on the signal received from each sensor and one or more selection criteria comprises automatically selecting the sensor(s) based on the absolute power and the relative power for each of the frequency bands for each sensor. In one embodiment, the set of frequency bands can all be within the range of 0.1 Hz to 235 Hz. For example, the set of frequency bands can comprise 0.1-4 Hz, 4-8 Hz, 8-13 Hz, 13-30 Hz, 0.1-30 Hz, 30-55 Hz, 65-115 Hz, 125-175 Hz, and 185-235 Hz. In other embodiments, the frequency bands can be above 235 Hz (e.g., up to 600 Hz, greater than 600 Hz, etc.). Note that the one or more processors 108 can decimate all frequency bands below 55 Hz prior to filtering the signal(s). The absolute power can be calculated using the using $$P_{Abs}(s, e_s, b, k) = \frac{1}{N}\sum_{1}^{N} V(n)^2 [\mu V^2],$$

and the relative power can be calculated using $$P_{Rel}(s, e_s, b, k) = \frac{P_{Abs}(s, e_s, b, k)}{\Sigma_{b=1}^{8} P_{Abs}(s, e_s, b, k)} [AU],$$

where s is a subject number, $e_s$ is one of the sensors, b is one of the frequency bands, k is an epoch of data, N is a number of data points in each epoch, and V(n) is an unipolar voltage at a given discrete time n in μV.

In some embodiments, one or more electrodes 118 communicably coupled to the one or more processors 108 via the sensor and/or electrode interface 102 can be used to provide an electrical stimulation to the brain. These electrodes can be the same or different than the sensors or electrodes used to detect the brain signals. The one or more processors 108 can select one or more of the electrodes 118 to provide the electrical stimulation. Moreover, the electrical stimulation can be provided in accordance with an electrical stimulation therapy. The one or more processors 108 can modulate the classified behavioral state using the electrical stimulation. An overall sleep-wake dynamic pattern can be fine tuned to meet a specified pre-determined behavioral state pattern. In addition, the one or more processors 108 can drive the classified behavioral state to a prescribed behavior state using the electrical stimulation. The system may also include a remote device communicably coupled to the one or more processors 108, in which the one or more processors 108 transmit the classified behavioral state to the remote device, and receive one or more control signals for the electrical stimulation from the remote device. The remote device can be a handheld device, a cloud computing resource, a computer or any other type of control or processing device.

Figure 3:
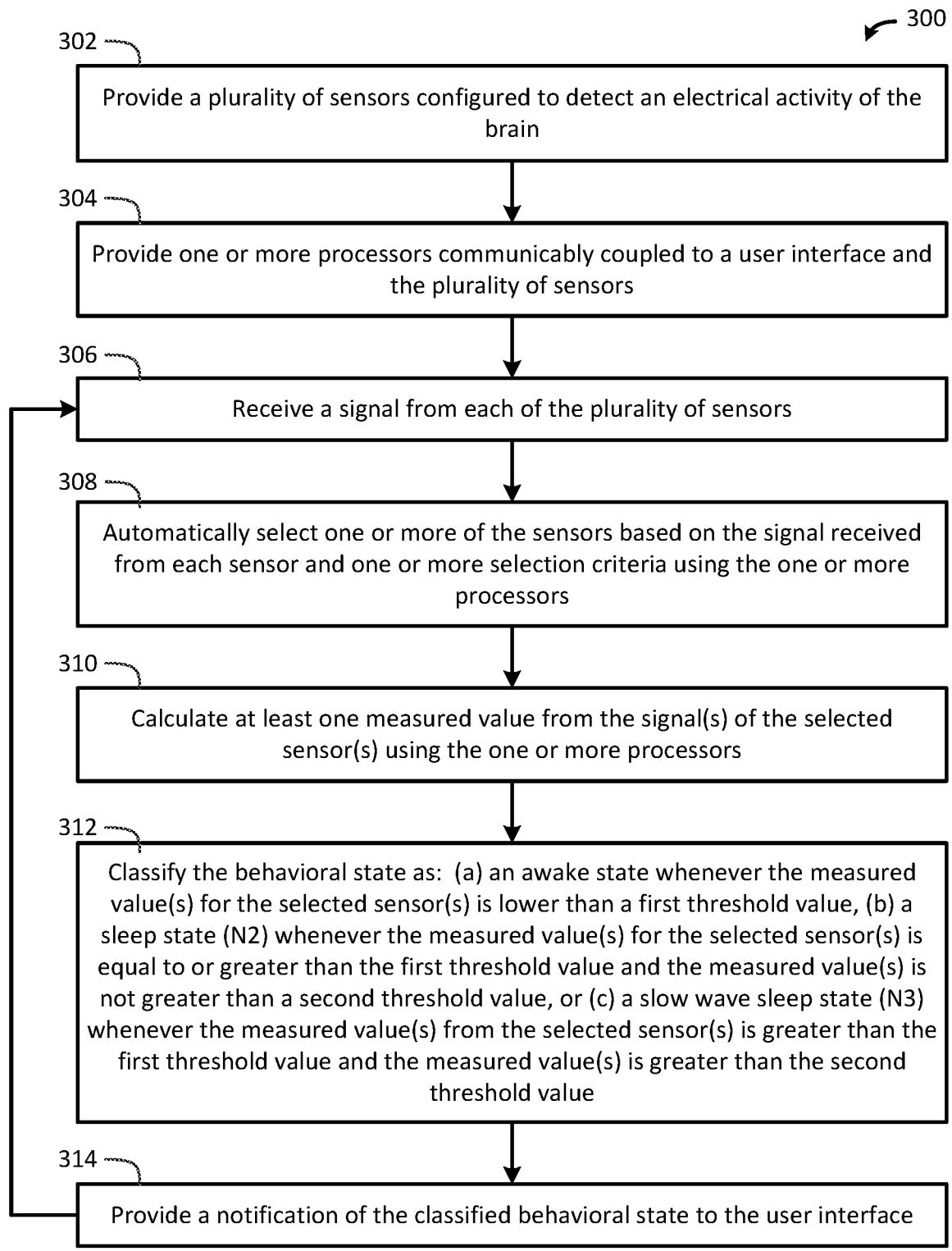
FIG. 3 is a flow chart of a method in accordance with one embodiment of the present invention.

Referring now to FIG. 3, a flow chart of a method 300 for classifying the behavioral state of the brain is shown in accordance with one embodiment of the present invention. A plurality of sensors 118 configured to detect an electrical activity of the brain are provided in block 302. One or more processors 108 communicably coupled to a user interface 104 and the plurality of sensors 118 are provided in block 304. A signal is received from each of the plurality of sensors 118 in block 306, one or more of the sensors 118 are automatically selected based on the signals received from each sensor 118 and one or more selection criteria using the one or more processors 108 in block 308, and at least one measured value is calculated from the signal(s) of the selected sensor(s) using the one or more processors 108 in block 310. The behavioral state is classified in block 312 as: (a) an awake state whenever the measured value(s) for the selected sensor(s) is lower than a first threshold value, (b) a sleep state (N1 or N2) whenever the measured value(s) for the selected sensor(s) is equal to or greater than the first threshold value and the measured value(s) is not greater than a second threshold value, or (c) a slow wave sleep state (N3) whenever the measured value(s) from the selected sensor(s) is greater than the first threshold value and the measured value(s) is greater than the second threshold value. Thereafter, a notification of the classified behavioral state is provided to the user interface 104 in block 314. The process is repeated (blocks 306-314) as necessary. Note that the method 300 can be implemented using a non-transitory computer readable medium that when executed causes the one or more processors to perform the method.

In some embodiments, the one or more processors 108 can also classify the brain behavioral state as a drowsy state (N1), a REM state, or a microstate within the drowsy state (N1), the sleep state (N2) or the slow wave sleep state (N3), or a brain state characterized by abundant or excessive pathological activity, or a brain state otherwise identified as representing an elevated probability for occurrence of a seizure. The microstate can be identified by $NJ_i$ where J=1, 2, 3 denotes the classically defined sleep states (N1, N2, N3) and i=1, 2, 3, ..., m denotes the microstates within each of the classically defined sleep states (N1, N2, N3). Moreover, the one or more processors 108 can store the classified behavioral state in the data storage or memory 106, provide an alert whenever the classified behavioral state is different than a previous classified behavioral state, and/or automatically map one or more spatial and temporal patterns of the classified behavioral state and one or more transitions between the classified behavioral states.

The one or more processors 108 can receive one or more configuration settings via the user interface 104. In some embodiments, the configuration settings can be a manual or automatic sensor selection, a preprocessing algorithm selection, a detection algorithm selection, a feature selection, a clustering method selection (e.g., K-NN, hierarchical trees, deep learning, neural networks, t-SNE, isomap, Sammon mapping, linear embedding, unsupervised deep embedding, etc.), or a thresholding rule selection. In some embodiments, the receiving, selecting, calculating, classifying and providing steps are performed by the one or more processors 108 using an operational mode comprising: a fully automated and unsupervised mode (e.g., FIG. 4); or a semi-automated mode; or an active learning mode—unsupervised first and supervised by redefining clusters displayed to user (user can reassign each part of the data into different class and retrain); or a supervised mode—fully supervised and trained by expert or trained on known scalp electrophysiology data in parallel with any simultaneous data (e.g. intracranial, epidural, subscalp, EEG, video recording, EMG, actigraphy, etc.); or other desired mode. Depending on the configuration used, the behavioral state can be classified without a gold standard scoring. The one or more processors 108 can also use training signal processing and a machine learning system to identify one or more suitable sensor configurations for an automated or semi-automated classification of the behavioral state. Moreover, the one or more processors 108 select target brain locations for the sensors from one or more of a cortex, hippocampus, thalamus, brain stem, basal ganglia, subthalamic nucleus, globus pallidus or other movement circuitry structures and muscles via EMG or ENG or actigraphy.

In some embodiments, the first threshold value comprises a first Delta power value (e.g., a median relative Delta, etc.) and the second threshold value comprises a second Delta power value (e.g., a $40^{th}$ percentile of the relative Delta, etc.). The one or more processors 108 can pre-process the signals by: detecting an abnormal amplitude distortion in the signals; or detecting a seizure or an abnormal electrophysiological condition using the signals; or detecting a high 60 or 50 Hz line interference in the signals; or other desired process. For example, the one or more processors 108 can select or restrict a number of channels of the sensors 118, or a number of power spectral features of the sensors 118. The one or more selection criteria can be: a power spectral features extraction; or a clustering algorithm (e.g., K-NN, hierarchical trees, deep learning, neural networks, t-SNE, isomap, Sammon mapping, linear embedding, unsupervised deep embedding, etc.); or one or more measures of separability; or other desired criteria. For example, the one or more selection criteria can be a K-NN clustering algorithm with Euclidean distance measure where inter and intra-cluster distance are used as parameters for selection of only one sensor. As will described below, only selecting one sensor can be beneficial and effective.

In some embodiments, the one or more processors 108 can filter the signal(s) into a set of frequency bands for each sensor, calculate an absolute power and a relative power for each of the frequency bands for each sensor, such that automatically selecting the sensor(s) based on the signal received from each sensor and one or more selection criteria comprises automatically selecting the sensor(s) based on the absolute power and the relative power for each of the frequency bands for each sensor. In one embodiment, the set of frequency bands can all be within the range of 0.1 Hz to 235 Hz. For example, the set of frequency bands can comprise 0.1-4 Hz, 4-8 Hz, 8-13 Hz, 13-30 Hz, 0.1-30 Hz, 30-55 Hz, 65-115 Hz, 125-175 Hz, and 185-235 Hz. In other embodiments, the frequency bands can be above 235 Hz (e.g., up to 600 Hz, greater than 600 Hz, etc.). Note that the one or more processors 108 can decimate all frequency bands below 55 Hz prior to filtering the signal(s). The absolute power can be calculated using the using $$P_{Abx}(s, e_s, b, k) = \frac{1}{N}\sum_{1}^{N} V(n)^2 [\mu V^2],$$

and the relative power can be calculated using $$P_{Rel}(s, e_s, b, k) = \frac{P_{Abs}(s, e_s, b, k)}{\Sigma_{b=1}^{8} P_{Abs}(s, e_s, b, k)} [AU],$$

where s is a subject number, $e_s$ is one of the sensors, b is one of the frequency bands, k is an epoch of data, N is a number of data points in each epoch, and V(n) is an unipolar voltage at a given discrete time n in μV.

In some embodiments, one or more electrodes 118 communicably coupled to the one or more processors 108 via the sensor and/or electrode interface 102 can be used to provide an electrical stimulation to the brain. These electrodes can be the same or different than the sensors or electrodes used to detect the brain signals. The one or more processors 108 can select one or more of the electrodes 118 to provide the electrical stimulation. Moreover, the electrical stimulation can be provided in accordance with an electrical stimulation therapy. The classified behavioral state can be modulated using the electrical stimulation. In addition, an overall sleep-wake dynamic can be fine tuned to meet a specified pre-determined behavioral state pattern. The electrical stimulation can be used to drive the classified behavioral state to a prescribed behavior state. The classified behavioral state can also be transmitted to a remote device, and one or more control signals for the electrical stimulation can be received from the remote device. The remote device can be a handheld device, a cloud computing resource, a computer or any other type of control or processing device.

Testing of the present invention and specific non-limiting examples thereof will now be described to show that human behavioral states can be classified into AW, N2, and N3 without any apriori knowledge and need for gold standard sleep scoring. Presented classification method uses iEEG (0.1-235 Hz) and fully automated unsupervised machine learning methods (such as K-means or hierarchical tree clustering). The method was tested using intracranial and simultaneous scalp EEG recording in patients undergoing evaluation for epilepsy surgery. It was demonstrated that using single iEEG channel can yield accurate automated classification of AW, N2, and N3 sleep stages, and it was evaluated by the gold standard, polysomnography (AASM rules 2012). Future implantable medical devices may benefit from accurate behavioral staging in and automated quantification of patient sleep patterns that can enable administration of behavioral-state-specific therapies. Particularly for epilepsy, such method can modulate seizure detection and increase performance forecasting algorithms.

Data were recorded from patients with drug resistant epilepsy undergoing evaluation for epilepsy surgery at Mayo Clinic Rochester, Minn. The Mayo Clinic Institutional Review Board approved the study. All subjects provided informed consent. The subjects underwent intracranial electrode implantation as part of their clinical evaluation for epilepsy surgery when non-invasive studies could not adequately localize the origin of seizure generation, i.e. seizure onset zone (SOZ).

Data from eight subjects with medial temporal lobe focal epilepsy was analyzed retrospectively. All subjects were implanted with intracranial depth electrodes, grids, and strips;

each depth electrode consisted of either 4 or 8 recording contacts, and all subjects had simultaneous scalp EEG recordings for sleep scoring including eye and chin electrodes.

Depth electrode arrays (AD-Tech Medical Inc, Racine, Wis.) consisted of a 1.3 mm diameter polyurethane shaft with Platinum/Iridium (Pt/Ir) clinical macroelectrode contacts. Each contact was 2.3 mm long with 10 mm center-to-center spacing (surface area 9.4 mm2 and impedance 200-500 Ohms). Anatomical localization of electrodes was achieved by co-registering post-implant CT data and co-registered to the patient's high-resolution MM using a normalized mutual information algorithm (SPM8, Wellcome Trust Centre for Neuroimaging). Electrode coordinates were then automatically labeled by using the SPM Anatomy toolbox, with an estimated accuracy of 5 mm (Tzourio-Mazoyer et al. 2002).

Post-implant CT images were co-registered to the patient's presurgical MRI. Illustrated is an occipital approach implant of mesial temporal lobe with an 8 contact depth electrode along the axis of the hippocampus in a patient with drug resistant epilepsy.

Neuralynx Cheetah electrophysiology system (Neuralynx Inc.) was used to acquire all iEEG data. A common reference, a stainless steel scalp suture placed in the vertex region of the scalp, was used midline between the international 10-20 Cz and Fz electrode positions. Data acquisition mode used a 9 kHz antialiasing analog filter, digitized at 32 kHz sampling rate, filtered by low pass zero phase shift 1 kHz antialiasing filter and down sampled to 5 kHz.

The SOZ electrodes and times of seizure onset were determined by identifying the electrodes with the earliest iEEG seizure discharge. Seizure onset times and zones were identified by visual review of iEEG recorded electrographic seizures, as described previously (Worrell et al. 2004; Warren et al. 2010; Klimes et al. 2016).

EEG recordings from scalp were bandpass filtered between 0.3 and 75 Hz, and 60 Hz notch filtered for scoring using third order linear phase Butterworth filters. Visual sleep scoring was in accordance with standard methods (AASM 2012) by a neurologist board-certified in sleep medicine (EKS) with modification for replacing the electrooculogram (EOG) recording with FP1, FP2, and FPZ scalp electrodes. Standard length of epoch (30 seconds) with no overlap was used for scoring (AASM 2012). Wakefulness was determined by the presence of eye blinks visualized in frontal scalp leads, accompanied by posteriorly dominant alpha rhythms (8-12 Hz) posteriorly, comprising >50% of the epoch. Slow-wave sleep (N3) was scored when high-voltage (>75 uV), low frequency delta (0.5-2 Hz) activity on scalp EEG was present in at least 20% of the epoch (i.e., at least 6 s within a 30 s epoch) in the frontal derivations using conventional International 10-20 System electrode placements (FP1, FP2, FZ, F3, F4, CZ, C3, C4, O1, O2, and Oz). A similar approach has been used in previous studies (Bower et al. 2015, Klimes et al. 2016, Kremen et al. 2017).

Continuous scalp and iEEG from each patient were manually reviewed using a custom MATLAB viewer (Brinkmann et al. 2009) prior automated analysis to account for channels and time segments containing significant artifacts, epileptiform discharges or seizures, these were not included in subsequent analysis.

All iEEG signals were filtered into eight frequency bands as follows: b={0.1-4 Hz,4-8 Hz,8-13 Hz,13-30 Hz,0.1-30 Hz,30-55 Hz,65-115 Hz,125-175 Hz,185-235 Hz}. All iEEG signals were filtered using 6th order bandpass Butterworth filters in a zero-phase filtering approach. In all frequency bands below 55 Hz, signals were decimated before applying the bandpass filter, to avoid filter instability. The relative spectral power in each frequency band was calculated for all electrodes across all subjects for each 30 second epoch, directly corresponding to the 30 second epochs sleep staged from scalp EEG. The absolute power was calculated first as an epoch average absolute energy of filtered time series defined by equation $$P_{Abs}(s,\ e_s,\ b,\ k) = \frac{1}{N}\sum_{n=1}^{N} V(n)^2\,[\mu V^2]$$

where s={1, ..., 8} is subject number, $e_s$={1, ... $\max_{1\le s\le 8} e_s$} is given electrode, b={1, ..., 8} is frequency band, k={1, ..., x} is epoch of data, N is the number of data points in each 30 second epoch, and V(n) is the unipolar voltage at given discrete time n in µV. Subsequently, the relative spectral power levels were calculated as follows:

$$P_{Rel}(s,\ e_s,\ b,\ k) = \frac{P_{Abs}(s,\ e_s,\ b,\ k)}{\sum_{b=1}^{8} P_{Abs}(s,\ e_s,\ b,\ k)}\,[AU]$$

to assess the ratio of each band power to power of all frequency bands (0.1-235 Hz). Note that 60 or 50 Hz line interference and its harmonics were avoided by band width selections of individual bands. The only relative power in bands was used as input of classifiers.

Figure 4:
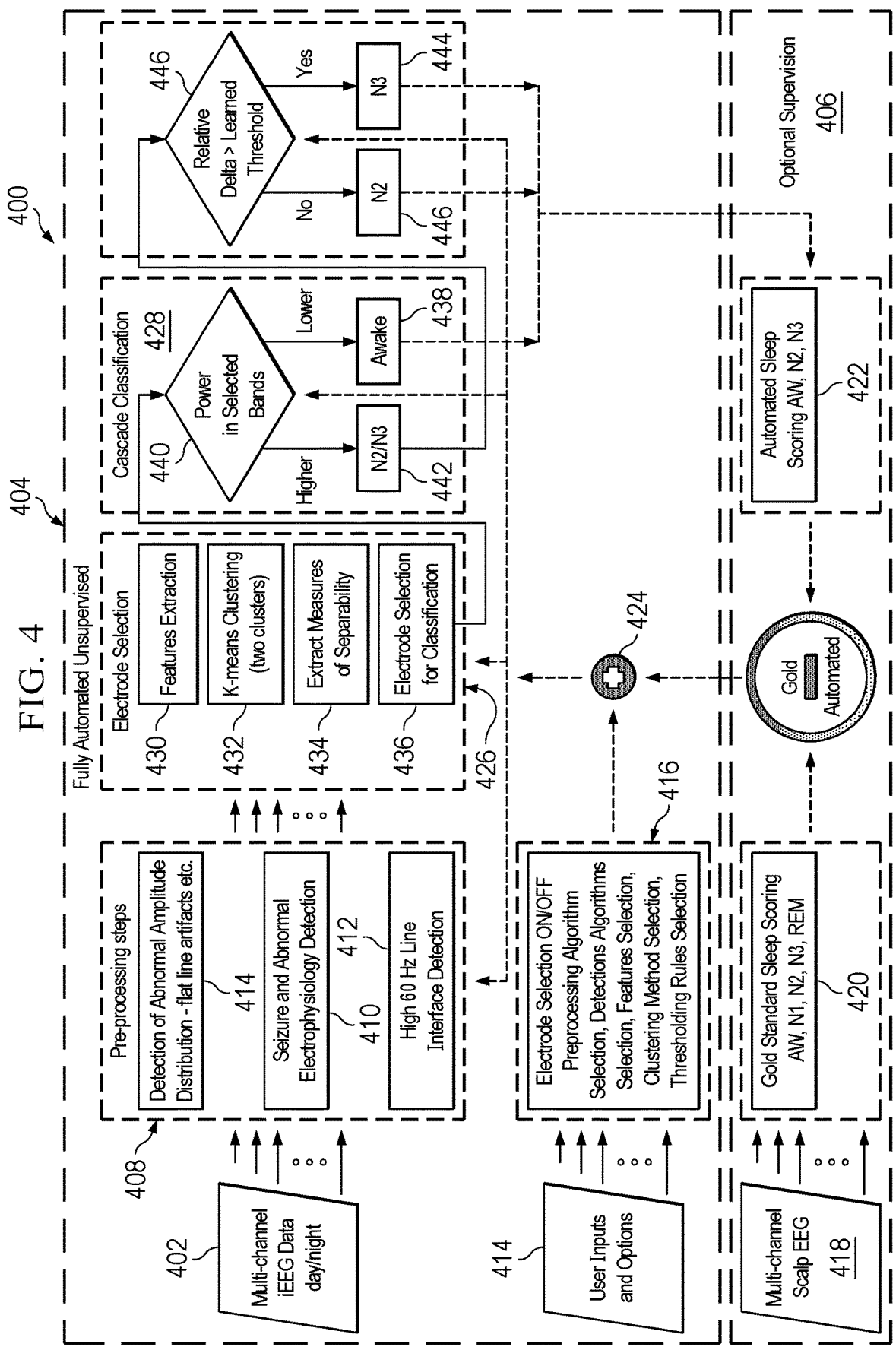
FIG. 4 is a flow chart of a method in accordance with another embodiment of the present invention.

Now referring to FIG. 4, a flow chart of a method 400 for classifying the behavioral state of the brain is shown in accordance with another embodiment of the present invention. The method 400 is also referred to as the Behavioral State Classifier (BSC). Sleep scoring and multi-channel iEEG data 402 are used in subsequent automated steps for feature extraction or selection (if turned on). The single electrode assesed to yield in the best performance is selected and used for classification and classifier uses features extracted from the selected electrode and then supplied to inputs of hierarchical clustering methods that returns an AW, N2, and N3 classification. The user can select and restrict the number of channels, number of features, and whether automated feature selection and electrode selection is used.

The top part 404 of FIG. 4 shows its unsupervised method that was trained and tested here in the study and it doesn't require training on gold standard data for each patient. The bottom part 406 of FIG. 4 shows how another user input and/or a supervision and active learning can be implemented if needed or if training data are being available. Here a day and night of multichannel iEEG recording were used as an input of the method for each patient. The method has several preprocessing steps 408 that can be used if configured, and that automatically detect seizures and abnormal electrophysiology 410 (Baldassano 2017), 60 or 50 Hz line noise 412, abnormal amplitude segments (e.g., flat line artifacts, etc.) 414 and discards them from further behavioral state analysis. Preprocessing steps 408 are followed by feature extraction steps. Definition of features and their selection is optional and can be configured in unsupervised version 404 and supervised version 406, and can be automatically adjust when gold standard data are present. In the unsupervised version 404, user inputs and options 414 are used define and select features 416, such as electrode selection ON/OFF, preprocessing algorithm selection, detections algorithms selection, features selection, clustering method selection, thresholding rules selection, and/or other inputs/options. In the supervised version 406, multi-channel scalp EEG data 418 is processed using gold standard sleep scoring (AW, N1, N2, N3, REM) 420 to define and select the features, and/or automated sleep scoring (AW, N2, N3) 422 from the cascade classification is used to define and select the features. As indicated by the dotted-lines, the defined and selected features are used to configure the pre-processing steps 408, the electrode selection 426 and the cascade classification 428. Electrode selection 426 may include features extraction 430, K-means clustering (two clusters) 432, extract measures of separability 434, electrode selection for classification 436, or other type of selection. Cascade classification 428 classifies the behavior state as Awake 438 if the power in the selected bands 440 is lower than a specified value, and as N2/N3 442 if it is higher. Following the N2/N3 442 classification, the behavior state is classified as N3 444 if the relative data is greater than a learned threshold 446, and as N2 446 if is not.

For this study, PIB features described above were used and the results are reported using solely these features. Based on available number of electrodes, method will extract all PIB features for each electrode and based on selected method of clustering and measures of separability and the method selects automatically a best suitable electrode for classification. All parameters in this step, such as methods of clustering, measures of separability, automated or manual selection of electrodes can be reset or bypassed by user input parameters. For example, user can hard reset the electrode or number of electrodes being used for classification. The reported results were obtained using K-NN clustering algorithm with Euclidean distance measure, where inter and intra-cluster distance are used as parameters for the automated selection of only one electrode. In next steps, cascade classifiers are deployed to differentiate first the AW from other behavioral states, and then state N2 from N3. Cascade classifiers use thresholding rules to assign clusters to a correct class. The classifier rules can be again redefined by user input or retrained by supervision and gold standard of sleep scoring if available. Here, the reported results were obtained using thresholding based on Delta power in first classifier to set cluster with lower mean Delta into AW. A sleep cluster then enters next classification step that is differentiating between N2 and N3 using heuristically set threshold of relative Delta band.

Continuous day/night recording was used on all subjects in data set. Only those nights with clean continuous recording were selected, no breaks in recording were present and no serious recording artefact or seizures during that period occurred, 60 Hz line interference noise was allowed in data to account for real conditions. Data of one randomly selected patient were used to validate heuristically suggested method and gently tune pre-processing steps and thresholds of classifier. Data from all eight patients were then used to test method and generate results.

Head to head comparison in each epoch was done to compare difference of gold standard sleep scoring and outputs of the method to objectively evaluate classifier and generate metrics of performance. Errors of classifier for each sleep stage were weighted based on the frequency of occurrence of each sleep stage in given patient. Thus, weighted measures of accuracy, sensitivity and specificity were generated for each sleep stage that was automatically classified by the method. Average results were also generated across all stages.

In total, eight days and nights of EEG and iEEG recorded from 8 subjects (40±11) years old, 3 females were analyzed. All patients selected for analysis had a medial temporal lobe epilepsy. Half of patient exhibits all know behavioral sleep stages during monitoring period so the analysis is done even including rapid eye movement (REM) sleep stages that our classifier is not able to classify and thus are counted as errors.

Data of one patient was used to double-check and optimize parts of the method that were originally set heuristically using a gold standard scoring rules such as thresholds of classifiers. During optimization, these settings did not have to be changed so the data is reported on cohort of whole 8 patients. In reported results, a fully unsupervised setting of the method was used with automated selection of one electrode using all extracted PIB features for following classification. Table 1 below shows overall performance of method on these data. The average errors are actually weighted errors so they are not influenced by unbalanced problem and thus biased by major class. In conclusion, more than 90% in each precision, sensitivity, and specificity was achieved for each analyzed patient. Note that for all patients with REM sleep stages, the average precision is lower and sensitivity and/or specificity is affected. Average amount of REM sleep from analyzed data was ~6%.

TABLE 1

Performance of the method across all behavioral states.
Weighted accuracy is shown to account for unbalanced data.
Patient that exhibit REM sleep stages as well are marked too.

| Patient Number | All classes [%] | Sensitivity [%] | Specificity [%] |
|---|---|---|---|
| 1 | 98 | 94 | 99 |
| 2 | 95 | 94 | 94 |
| 3 | 96 | 99 | 92 |
| 4 (REM) | 92 | 92 | 91 |
| 5 (REM) | 92 | 87 | 94 |
| 6 (REM) | 92 | 96 | 90 |
| 7 | 97 | 98 | 96 |
| 8 (REM) | 92 | 94 | 90 |
| Average | 94 | 94 | 93 |

Dissected performance of algorithm in sleep is shown in Table 2. Classification accuracy, sensitivity, and specificity are compared for N2 and N3 to show feasibility of such classifier for analysis of sleep phases that is often of interest in neuroscience and neurology. The method as tested, fails more in N2 sleep stage, while N3 has very good performance, high specificity and method is stable across patients. Sensitivity of the tested settings of the method in N2 phase is probably affected by misclassifying N2 as N1 or N3, while still retaining high specificity. This translated means that automatically picked up N2 is from 97% real N2 phase, while for N3 it is 94%. Note that REM patients has similar performance in automated N2 and N3 scoring. That is because PIB features in REM are very similar to PIB features in AW and majority of REM is thus classified as AW.

TABLE 2

Performance of algorithm in N2 and N3 sleep phases only. Again,
weighted accuracy is accounting for class imbalance problem.
Patients that exhibit REM sleep stages are marked.

| Patient Number | N3 Accuracy [%] | Sensitivity [%] | Specificity [%] | N2 Accuracy [%] | Sensitivity [%] | Specificity [%] |
|---|---|---|---|---|---|---|
| 1 | 97 | 95 | 97 | 87 | 77 | 98 |
| 2 | 95 | 94 | 94 | 87 | 80 | 96 |
| 3 | 96 | 99 | 92 | 87 | 78 | 95 |
| 4 (REM | 95 | 95 | 93 | 90 | 84 | 97 |
| 5 (REM) | 98 | 97 | 98 | 83 | 69 | 98 |
| 6 (REM) | 94 | 95 | 93 | 89 | 83 | 95 |
| 7 | 98 | 99 | 96 | 89 | 81 | 98 |
| 8 (REM) | 93 | 99 | 86 | 88 | 78 | 97 |
| Average | 96 | 97 | 94 | 88 | 78 | 97 |

Figure 5:
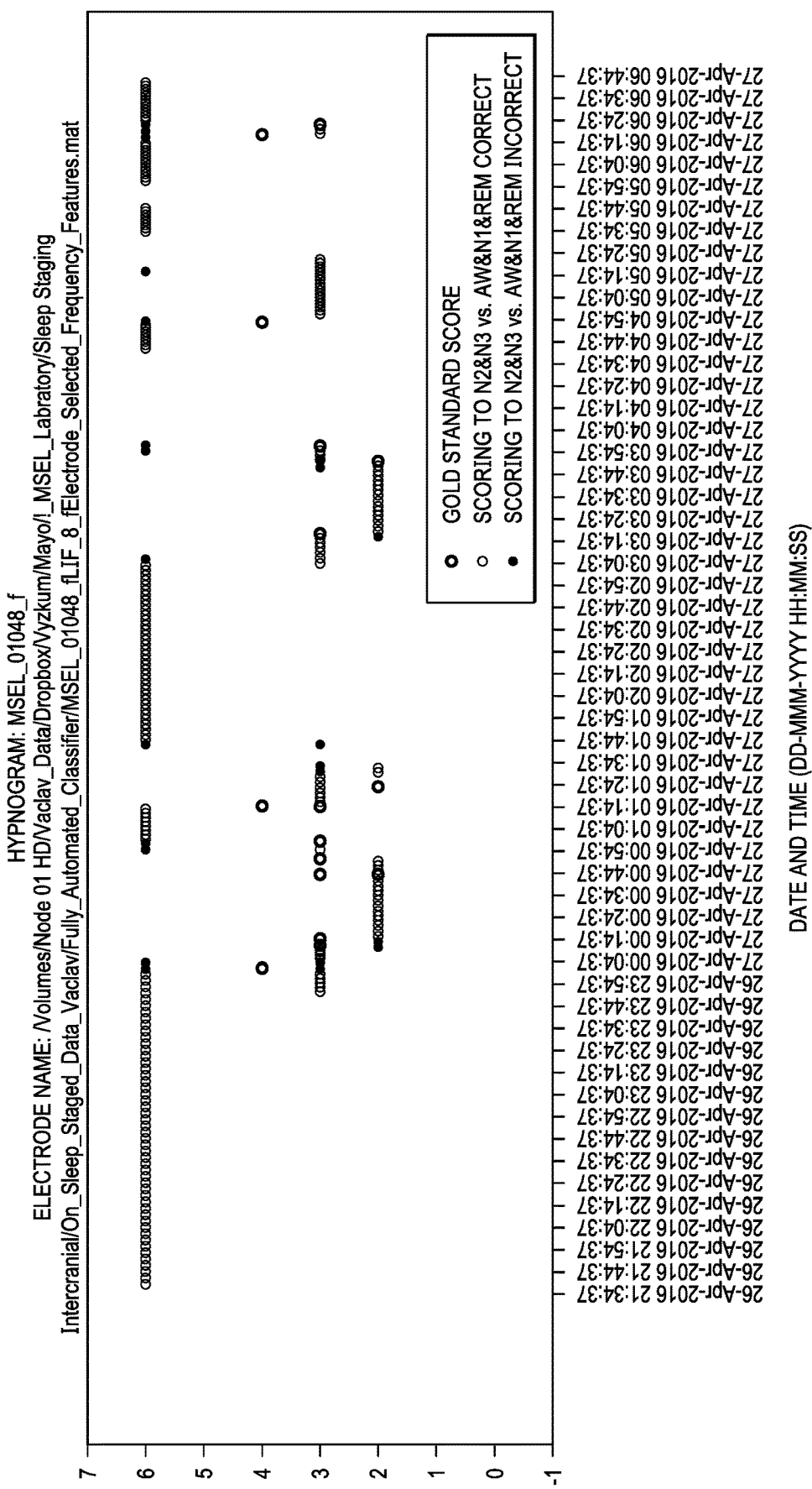
FIG. 5 is a graph showing results of an automated classification of AW, N2, N3 of a patient using one night data in accordance with another embodiment of the present invention.

For a demonstration, data of classification was selected from a night of patient one as demonstration of classification (FIG. 5) showing results of classification approximately from 9 PM to 7 AM in the morning. It is fairly visible that for this patient the method fails to classify transitions between gold standard sleep stages such as AW-N1-N2 that is by the design of cascade classifier that only picks up AW/N2/N3. Also, transitions of N2-N3 and N3-N2 or N2-AW are misclassified and classifier picks correct phase either little earlier or later. Stable and middle parts of sleep stages are usually classified correctly even for faster changes in sleep profile. Using FIG. 6, a profile is shown of extracted features from the same night shown on FIG. 5, where there is noticeable change of low frequency feature (Delta) during deeper phases of sleep (according to gold standard data), while higher frequencies are attenuated during sleep and of higher power in awake for given analyses on electrode that was automatically selected by the method. More specifically, each point in FIG. 5 shows epoch classified and compared to gold standard scoring. The green dots show correct classification, red dots show epoch that were misclassified, while orange dots mark what should be a correct classification.

Figure 6:
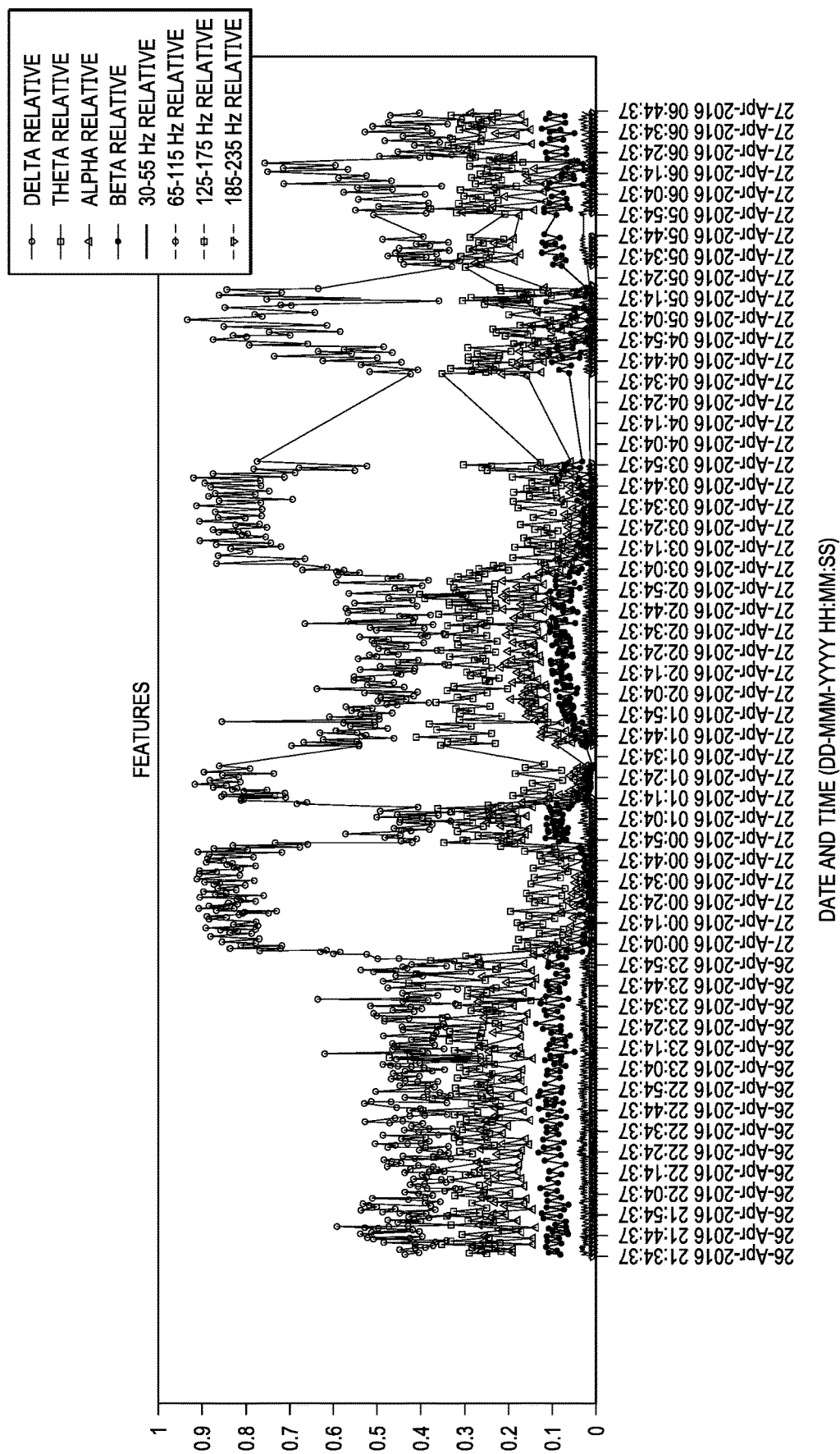
FIG. 6 is a graph showing scaled absolute features used for an automated classification of AW, N2, N3 of a patient using one night data.

FIG. 6 shows scaled absolute features used for an automated classification of AW, N2, N3 of patient number one using one night data from ~9 PM to ~7 AM using in FIG. 4. Low frequency features are scaled higher, while high frequency features stay low (known also as Power low).

The foregoing testing investigated behavioral state classification (wake & N2, and slow wave sleep) using intracranial EEG spectral power features in an unsupervised machine learning method. The method automatically selects one electrodes from array of available electrodes based on unsupervised score of the data and deploys cascade of classifiers using features extracted from selected electrode to classify into AW, N2, and N3 stages. The approach achieved high accuracy (94%) and performance (sensitivity 94% and specificity 93%). The results show that the method is significantly more specific to classify N2 (specificity 94%) and N3 (specificity 97) stages. Future implantable devices for epilepsy may benefit from accurate sleep/wake staging in order to quantify patient sleep patterns, give behavioral state specific therapies, and adjust seizure forecasting classifiers.

Figure 7:
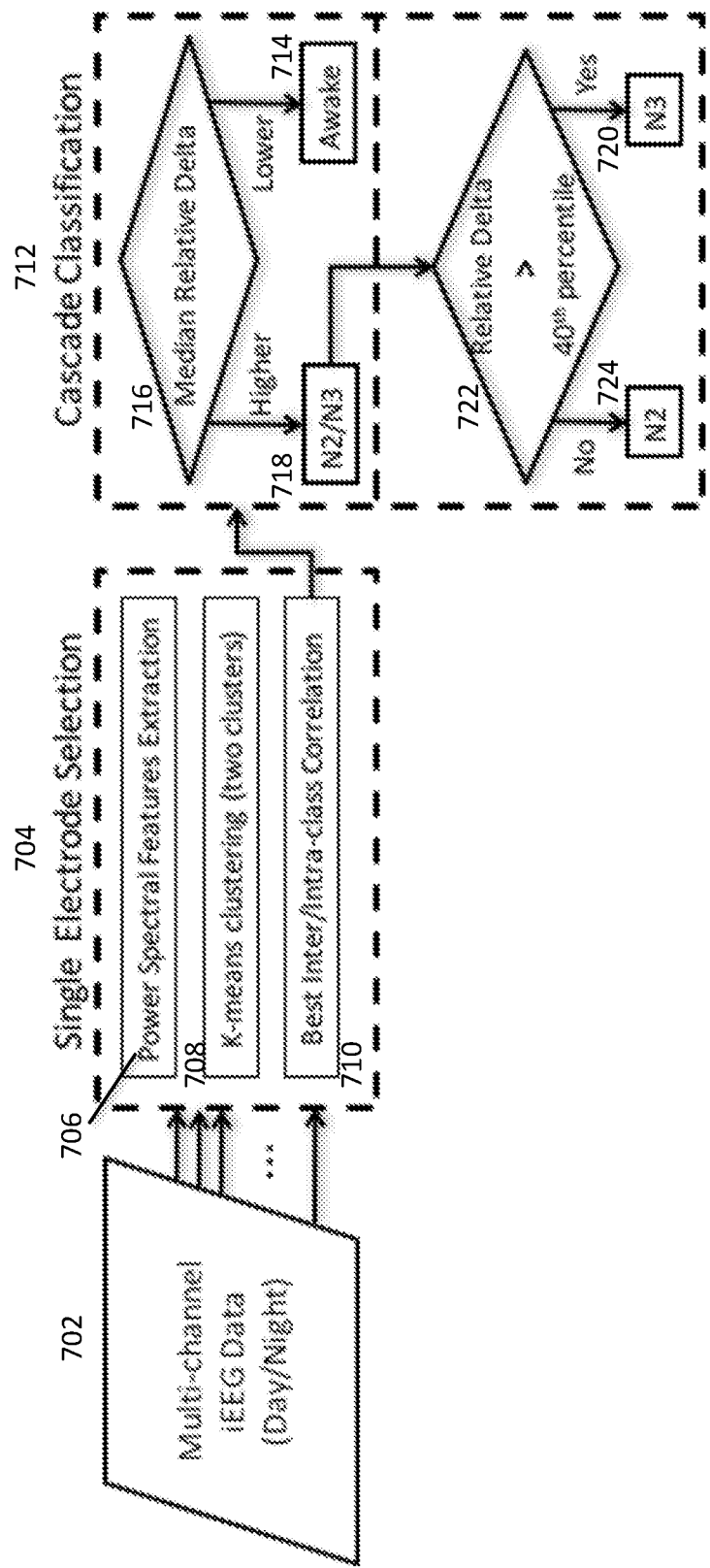
FIG. 7 is a flow chart of a method in accordance with another embodiment of the present invention.

FIG. 7 is a flow chart of a method 700 in accordance with another embodiment of the present invention. This method is an example of a fully automated unsupervised method for electrophysiology sleep staging using subscalp, epidural or intracranial EEG data. A signal from each of the plurality of sensors (multi-channel iEEG Data (Day/Night)) in block 702. A single sensor (e.g., electrode) is selected in block 704 based on the signals received from each sensor and one or more selection criteria using the one or more processor. The selection criteria used in block 704 may include power spectral feature extraction 706, K-means clustering (two clusters) 708, or best inter/intra-class correlation 710. At least one measured value from the signal(s) of the selected sensor(s) using the one or more processors and is used to classify the behavioral state in block 712. Cascade classification classifies the behavior state as Awake 714 if the measured value is lower than a median relative data 716, and as N2/N3 718 if the measured value is higher than the median relative data 716. Following the N2/N3 718 classification, the behavior state is classified as N3 720 if the relative data is greater than the $40^{th}$ percentile 722, and as N2 724 if the relative data is less than or equal to the $40^{th}$ percentile 722.

Figure 8:
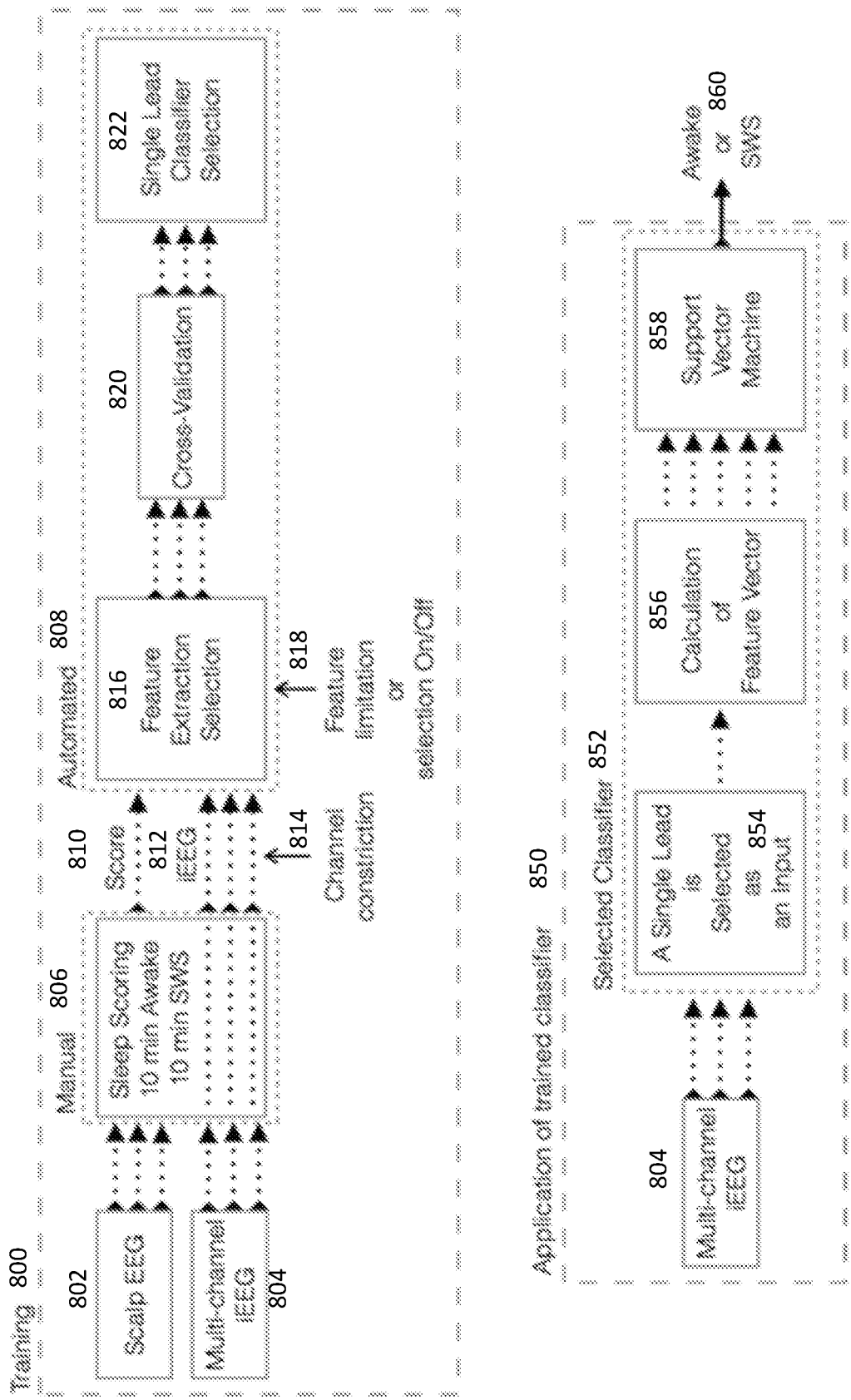
FIG. 8 is a flow chart of a method in accordance with another embodiment of the present invention.

FIG. 8 is a flow chart of a method in accordance with another embodiment of the present invention. This method is an example of a possible supervised version. Here iEEG is intracranial EEG data, but same approach applies to subscalp, epidural or intracranial EEG data. More specifically, FIG. 8 shows a training method 800 and an application of trained classifier 850. In training 800, scalp EEG data 802 and multi-channel iEEG data 804 is provided for manual sleep scoring (e.g., 10 min Awake, 10 min SWS) 806. Automated classification 808 uses the score 810 and iEEG data 812 with channel constriction 814 for feature extraction selection 816. Feature limitation or selection 818 can be on or off. The resulting feature extraction selection 816 is cross-validated in block 820 and single lead classifier selection is performed in block 822. The application of the trained classifier 850 uses the selected classifier 852 to process the multi-channel iEEG data 804. A single lead is selected as an input in block 854, feature vectors are calculated in block 856 and a support vector machine 858 is used in block 858 to classify the behavior state as Awake or SWS 860.

Figure 9:
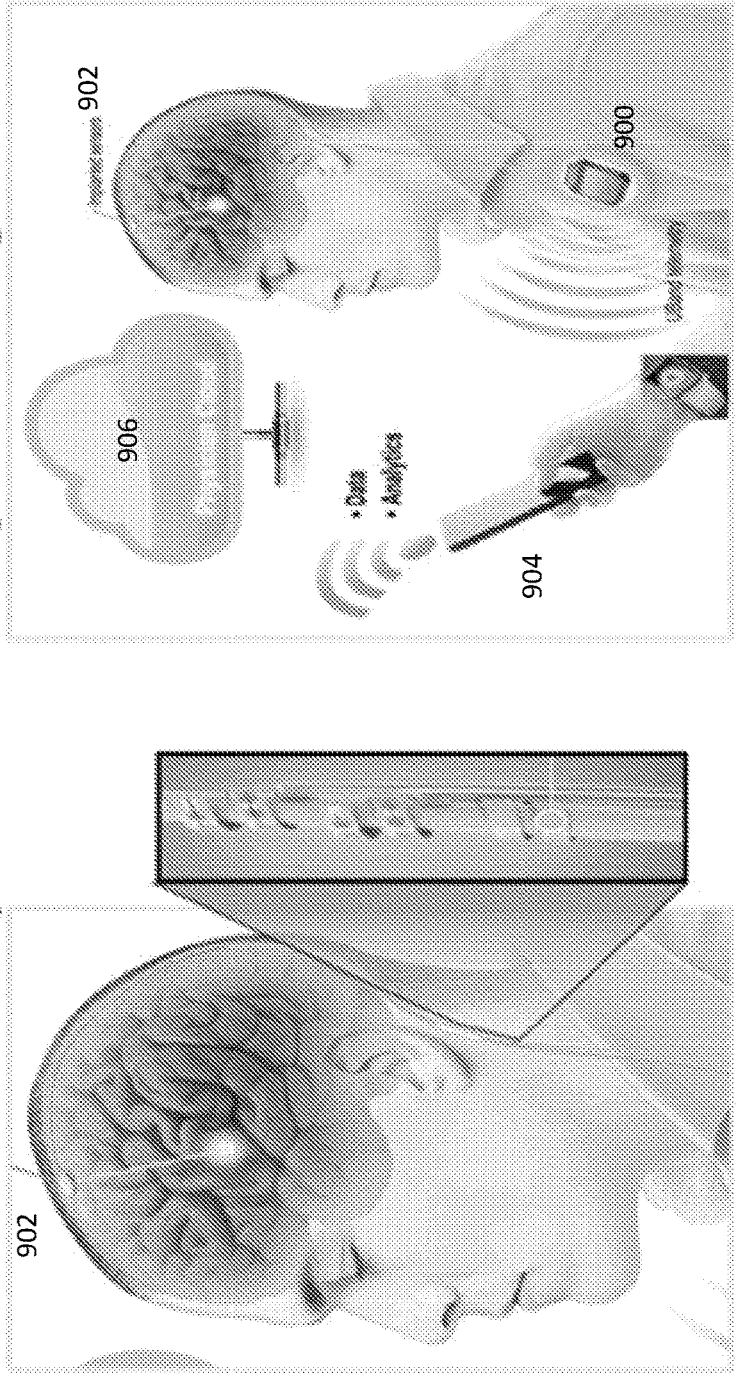
FIG. 9 is an illustration of a system that integrates an implanted device with brain electrodes and preipheral nerve electrodes, or wearable sensors (e.g., watch) that provides both sensing and electrical stimulation and couples this capability with a bi-directional connectivity with a handheld device and cloud computing environment.
Figure 10:
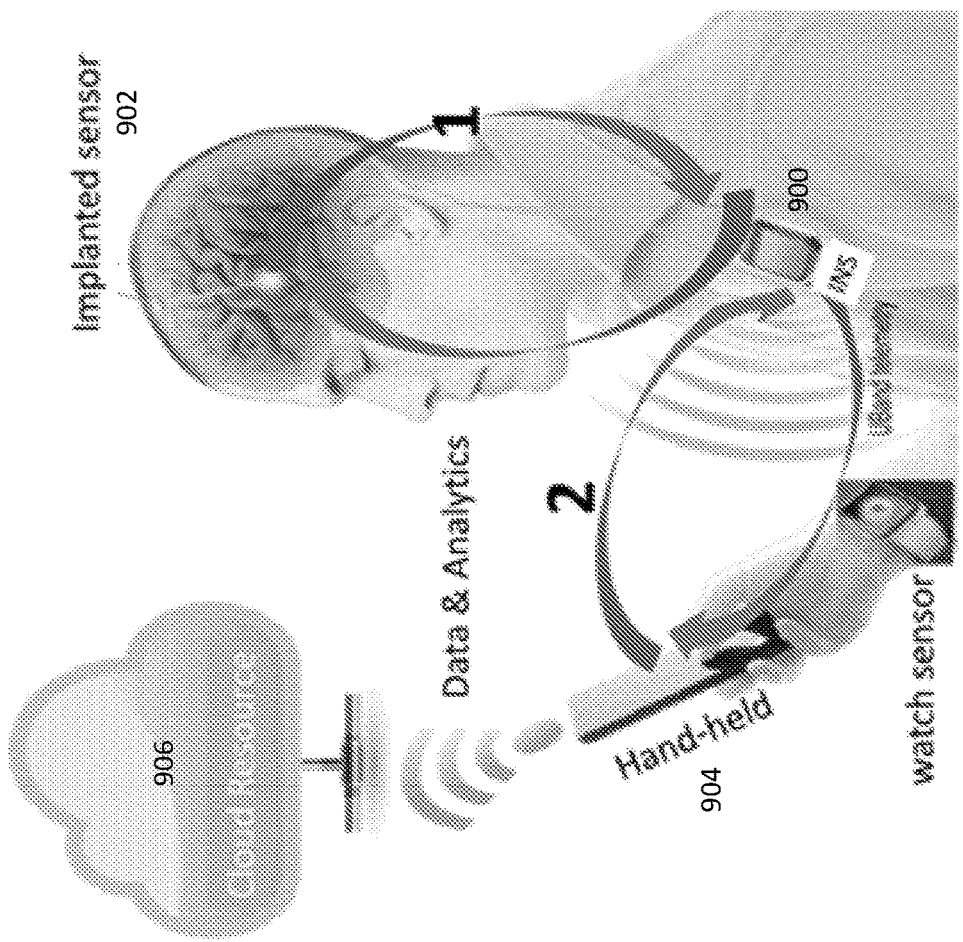
FIG. 10 is an illustration of how the system shown in FIG. 9 can be used in an application whereby measured signals from the brain and/or the peripheral system are analyzed to determine brain state (e.g. physiological (wake/sleep) or pathological) and used as inputs into a control-law application running on the implanted device (short latency stimulation=1), or the hand-held, or in the cloud (long latency=2).

The technology for brain state (behavioral state) determination and tracking described above can be used to dynamically follow and modulate brain state using electrical stimulation. As illustrated in FIGS. 9 and 10, the closed-loop system can modulate sleep and wake states using electrical stimulation, and fine-tune overall sleep-wake dynamics to meet any desired, pre-determined behavioral state patterns by tracking behavioral state and modulating via a control algorithm. For example, sleep quality, characteristics, and patterns can be improved to achieve clinical benefits for patients with sleep disorders.

The complete system can track behavioral state and this be used as an input into a control algorithm that uses electrical stimulation to modulate sleep and wake states, and fine tune overall sleep-wake dynamics to meet any desired, pre-determined behavioral state patterns. By tracking behavioral state and modulating brain state via a control algorithm it is possible drive the brain to the desired, prescribed brain state. For example, sleep quality, characteristics, and patterns can be improved to achieve clinical benefits for patients with sleep disorders. The control algorithm in this case would use behavioral state classifications determined from EEG or other sensors as the input and electrical stimulation is used to modulate and drive the brain to the prescribed state. This algorithm can run on the implanted device (for control algorithm with low computational complexity and short latency response), on the handheld device, or even in the cloud environment (for algorithms requiring more computational power & tolerating longer latency response).

FIG. 9 is an embodiment and application of proposed system that integrates an implanted device 900 with brain electrodes and peripheral nerve electrodes 902 that provides both sensing and electrical stimulation and couples this capability with a bi-directional connectivity with a handheld device 904 and cloud computing environment 906.

FIG. 10 is an illustration of how the system shown in FIG. 9 can be used in an application whereby measured signals from the brain and/or the peripheral system are analyzed to determine brain state (e.g. physiological (wake/sleep) or pathological) an used as inputs into a control-law application running on the implanted device (short latency stimulation=1) 900, or the hand-held 904, or in the cloud (long latency=2) 906. The implanted device 900 enables electrical stimulations via sensors 902 to drive the measured activity to a predetermined brain state.

The system for sensing can be a pluarity of implanted and wearable electrodes and sensors that communicate and interface with a tablet, phone, implantable device or cloud resource, or all of these integrated together creating a brain co-processor system (see for example, Kremen, V., Brinkmann, B. H., Kim, I., Guragain, H., Nasseri, M., Magee, A. L., . . . Worrell, G. A. (2018). Integrating brain implants with local and distributed computing devices: A next generation epilepsy management system. *IEEE J Transl Eng Health Med*, 6, 2500112. doi:10.1109/JTEHM.2018.286939)

There are many applications for an automated behavioral state classification system, such as the present invention, that can be integrated with an implantable device and used to control therapy delivery to specific brain behavioral states for modulating neuronal networks. Below are a few example applications, but those skilled in neurological devices and management of human health and disease will identify additional examples of brain state specific therapy that is made possible with automated behavioral state classification. Examples include:

Sleep quality monitoring in health and disease. Example application is quantifying sleep structure and duration using automated behavioral state classification. The output provides a continuous index of sleep quality based on age control population normal for sleep architecture and duration.

Brain State dependent Therapy in Neurological disease.
  Parkinson's Disease and other movement disorders involving Deep Brain Stimulation. Currently over 100,000 thousand people are implanted with Deep Brain Stimulators. The quality type and severity of tremors and other associated motor symptoms of both essential tremor, dystonia, and Parkinson's Disease has a sleep-wake variance which is important to characterize and inform with next-generation devices that should be changing their parameters of stimulation accordingly based on the behavioral state of a given patient.
  Application in epilepsy whereby electrical stimulation delivery is controlled by automated sleep staging. Recent research suggests that stimulation during post-seizure slow-wave (N2, N3) sleep could disrupt epilepsy engrams, reduce number of seizures, and prevent epilepsy progression. The approach may make it possible to prevent epilepsy from developing in patients who have suffered traumatic brain injury.
  Application in epilepsy whereby electrical stimulation delivery is controlled by automated sleep staging to target seizure generation that begin specifically out of a given brain state in order to prevent seizure initiation.
  Application to movement disorders—changing stimulation pattern based on automated sleep staging to prevent stimulation during night when it is not needed to extend device battery.

Cognition & Learning enhancement is facilitated by electrical stimulation to modulate different sleep stages. For example, enhance slow-wave sleep with electrical stimulation which has been shown to improve memory and motor task performance. Diseases leading to impairment in memory and cognition (e.g. Alzheimer disease) will benefit in modulation of learning & memory networks using behavioral state dependent therapeutic stimulation. Similarly, disruption of pathological learning and memory, such as seen in post-traumatic stress disorder (PTSD), using electrical stimulation controlled by brain behavioral state classifier to disrupt slow wave sleep that is critical to memory consolidation and learning Mood disorders, such as depression are associated with circadian rhythms. The use of brain behavioral state classification would allow rigorous tracking of circadian disruption and can be used to selectively deliver therapy and monitor success of therapy with behavioral state and sleep architecture quantification as an objective biomarker Narcolepsy could be managed by changing stimulation pattern automatically based on sleep staging to prevent human from transitioning into pathological REM sleep state unintentionally.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Agarwal, R., & Gotman, J. (2002). Digital tools in polysomnography. *Journal of Clinical Neurophysiology: Official Publication of the American Electroencephalographic Society*, 19(2), 136-43. http://doi.org/10.1097/00004691-200203000-00004.
2. Andrillon, T., Nir, Y., Staba, R. J., Ferrarelli, F., Cirelli, C., Tononi, G., & Fried, I. (2011). Sleep Spindles in Humans: Insights from Intracranial EEG and Unit Recordings. *Journal of Neuroscience*, 31(49), 17821-17834. http://doi.org/10.1523/JNEUROSCI.2604-11.2011.
3. Amir, N., & Gath, I. (1989). Segmentation of EEG during sleep using time-varying autoregressive modeling. *Biological Cybernetics*, 61(6), 447-455. http://doi.org/10.1007/BF02414906.
4. Baldassano S N, Brinkmann B H, Ung H, Blevins T, Conrad E C, Leyde K, Cook M J, Khambhati A N, Wagenaar J B, Worrell G A. Crowdsourcing seizure detection: algorithm development and validation on human implanted device recordings. Brain. 2017; 140(6): 1680-91.
5. Bergey G K, Morrell M J, Mizrahi E M, Goldman A, King-Stephens D, Nair D, et al. Long-term treatment with responsive brain stimulation in adults with refractory partial seizures. Neurology. 2015; 84:810-7.
6. Botella-Soler V, Valderrama M, Crépon B, Navarro V, Le Van Quyen M. (2012). Large-scale cortical dynamics of sleep slow waves. *PLoS One*, 7(2):e30757. doi: 10.1371/journal.pone.0030757. Epub 2012 Feb. 17. PMID: 22363484.

7. Bower M R, Stead M, Bower R S, Kucewicz M T, Sulc V, Cimbalnik J, . . . Worrell G A (2015). Evidence for Consolidation of Neuronal Assemblies after Seizures in Humans. *Journal of Neuroscience,* 35(3), 999-1010. doi: 10.1523/JNEUROSCI.3019-14.2015.
8. Bower M R, Kucewicz M T, St Louis E K, Meyer F B, Marsh W R, Stead M, Worrell G A. Reactivation of seizure-related changes to interictal spike shape and synchrony during postseizure sleep in patients. Epilepsia. 2017; 58:94-104.
9. Bragin, A., Wilson, C. L., Staba, R. J., Reddick, M., et al. (2002). Interictal high-frequency oscillations (80-500 Hz) in the human epileptic brain: entorhinal cortex. *Ann Neurol,* 52, 407-415.
10. Brinkmann B H, Bower M R, Stengel K A, Worrell G A, Stead M. (2009). Large-scale electrophysiology: acquisition, compression, encryption, and storage of big data. *J Neurosci Methods,* 180: 185-192.
11. Brinkmann B H, Patterson E E, Vite C, Vasoli V M, Crepeau D, et al. (2015). Forecasting Seizures Using Intracranial EEG Measures and SVM in Naturally Occurring Canine Epilepsy. *PLoS One,* 10(8): e0133900. doi: 10.1371/journal.pone.0133900.
12. Brinkmann B H, Wagenaar J, Abbot D, Adkins P, Bosshard S C, Chen M, Tieng Q M, He J, Muñoz-Almaraz F J, Botella-Rocamora P. (2016). *Crowdsourcing reproducible seizure forecasting in human and canine epilepsy. Brain,* 139:1713-1722.
13. Buzsaki, G. (2006). *Rhythms of the Brain* (Oxford University Press).
14. Cantero J L, Atienza M, Stickgold R, Kahana M J, Madsen J R, Kocsis B (2003) Sleep-dependent theta oscillations in the human hippocampus and neocortex. J Neurosci 23:10897-10903.
15. Cash, S. S., Halgren, E., Dehghani, N., Rossetti, A. O., et al. (2009). The human K-complex represents an isolated cortical down-state. *Science,* 324, 1084-1087.
16. Cook M J, O'Brien T J, Berkovic S F, Murphy M, Morokoff A, Fabinyi G, D'Souza W, Yerra R, Archer J, Litewka L, Hosking S, Lightfoot P, Ruedebusch V, Sheffield W D, Snyder D, Leyde K, Himes D. (2013). Prediction of seizure likelihood with a long-term, implanted seizure advisory system in patients with drug-resistant epilepsy: a first-in-man study. *Lancet Neurol,* 12:563-571.
17. Corsi-Cabrera M, Velasco F, Del Rio-Portilla Y, Armony J L, Trejo-Martinez D, Guevara M A, Velasco A L. Human amygdala activation during rapid eye movements of rapid eye movement sleep: an intracranial study. J Sleep Res. 2016 October; 25(5):576-582.
18. Cortes, C.; Vapnik, V. (1995). "Support-vector networks". *Machine Learning* 20 (3): 273. doi:10.1007/BF00994018.
19. Csercsa, R., Dombovári, B., Fabó, D., Wittner, L., et al. (2010). Laminar analysis of slow wave activity in humans. *Brain* 133, 2814-2829.
20. Danker-Hopfe, Anderer P, Zeitlhofer J, Boeck M, Dorn H, Gruber G, Heller E, Loretz E, Moser D, Parapatics S, Saletu B, Schmidt A, Dorffner G. (2009). Interrater reliability for sleep scoring according to the Rechtschaffen & Kales and the new AASM standard. *J Sleep Res., March;* 18(1):74-84. doi: 10.1111/j.1365-2869.2008.00700.x.
21. Eugster L1, Bargiotas P1, Bassetti CL1, Michael Schuepbach WM2. Parkinsonism Relat Disord. 2016 November; 32:12-19. doi: 10.1016/j.parkreldis.2016.08.006. Epub 2016 Aug. 7.Deep brain stimulation and sleep-wake functions in Parkinson's disease: A systematic review.
22. Ferrara M, Moroni F, De Gennaro L, Nobili L. Hippocampal sleep features: relations to human memory function. *Front Neurol.* 2012 Apr. 17; 3:57.
23. Ferrara M, De Gennaro L. (2011). Going local: insights from EEG and stereo-EEG studies of the human sleep-wake cycle. *Curr Top Med Chem.,* 11(19):2423-37.
24. Ferri R, Ferri P, Colognola R M, Petrella M A, Musumeci S A, Bergonzi P. (1989). Comparison between the results of an automatic and a visual scoring of sleep EEG recordings. *Sleep,* 12:354-62.
25. Funk C M, Honjoh S, Rodriguez A V, Cirelli C, Tononi G. Local Slow Waves in Superficial Layers of Primary Cortical Areas during REM. Sleep. Curr Biol. 2016 Feb. 8; 26(3):396-403.
26. Hastie, Tibshirani and Friedman (2009). The Elements of Statistical Learning (2nd edition). Springer-Verlag.
27. Haustein W, Pilcher J, Klink J, Schulz H. (1986). Automatic analysis overcomes limitations of sleep stage scoring. *Electroencephalogr Clin Neurophysiol,* 64:364-74.
28. He, B. J., Zempel, J. M., Snyder, A. Z., and Raichle, M. E. (2010). The temporal structures and functional significance of scale-free brain activity. *Neuron* 66, 353-369.
29. Hu S, Stead M, Dai Q, Worrell G A. (2010). On the recording reference contribution to EEG correlation, phase synchorony, and coherence. *IEEE Transactions on Systems, Man, and Cybernetics, Part B: Cybernetics,* 40(5), 1294-1304. doi:10.1109/TSMCB.2009.2037237.
30. Iber, C., Ancoli-Israel, S. and Chesson, A. and Quan, S. F. (2007) for the American Academy of Sleep Medicine. The AASM Manual for the Scoring of Sleep and Associated Events: Rules, Terminology and Technical Specifications, American Academy of Sleep Medicine, Westchester, Ill.
31. Kaplan A, Röschke J, Darkhovsky B, Fell J. (2001). Macrostructural EEG characterization based on nonparametric change point segmentation: application to sleep analysis. *J Neurosci Methods.,* 106:81-90.
32. Kemp B. A proposal for computer-based sleep/wake analysis. (1993). Consensus report. *J Sleep Res.,* 2:179-85.
33. Kelsey M, Politte D, Verner R, Zempel J M, Nolan T, Babajani-Feremi A, Prior F, Larson-Prior L J. (2012). Determination of neural state classification metrics from the power spectrum of human ECoG. *Conf Proc IEEE Eng Med Biol Soc.,* 2012:4336-40. doi: 10.1109/EMBC.2012.6346926.
34. Klimes P, Duque J J, Brinkmann B, Gompel J V, Stead S M, St Louis E K, Halamek J, Jurak P, Worrell G A. (2016). The Functional Organization of Human Epileptic Hippocampus. *J Neurophysiol., March* 30:jn.00089.2016. doi: 10.1152/jn.00089.2016.
35. Kremen V, Duque J, Brinkmann B H, Berry B M, Kucewicz M T, Khadjevand F, Van Gompel J, Stead S M, St Louis E, Worrell G A (2017). Behavioral State Classification in Epileptic Brain using Intracranial Electrophysiology. *Journal of Neural Engineering, Vol.* 14(2), January 2017.
36. Le Van Quyen M, et Al., (2010). Large-scale microelectrode recordings of high-frequency gamma oscillations in human cortex during sleep. *JNEUROSCI.* 5049-09.
37. Lee H and Choi S. (2003). PCA+HMNI+SVM for EEG pattern classification, *7th Proc. Int. Symp. on Signal Processing and Its Applications,* vol 1 pp 541-4.
38. Lehmann, D., Ozaki, Ho., and Pal, I. (1987). EEG alpha map series: brain micro-space-oriented adaptive segmen- 39. Leminen M M, Virkkala J, Saure E, Paajanen T, Zee P C, Santostasi G, Hublin C, Müller K, Porkka-Heiskanen T, Huotilainen M, Paunio T. (2017) Enhanced Memory Consolidation Via Automatic Sound Stimulation During Non-REM Sleep. *Sleep*. March 1; 40(3).

40. Liu C, Zhao H B, Li C S and Wang H. (2010). Classification of ECoG motor imagery tasks based on CSP and SVM. *BMEI: 3rd Int. Conf. on Biomedical Engineering and Informatics*, vol 2 pp 804-7.

41. Loomis A. L.; Harvey E. N.; Hobart G. A. (1937). Cerebral states during sleep as studies by human brain potentials. *J Exp Psychol* 21: 127-44.doi:10.1037/h0057431.

42. Lundstrom, B. N., Van Gompel, J., Britton, J., Nickels, K., Wetjen, N., Worrell, G., & Stead, M. (2016). Chronic Subthreshold Cortical Stimulation to Treat Focal Epilepsy. *JAMA Neurology*, 73(11):1370-1372. doi: 10.1001/jamaneurol.2016.2857.

43. McGaugh J L. Memory—a century of consolidation. *Science*. 2000; 287:248-51.

44. Nir, Y., Staba, R. J., Andrillon, T., Vyazovskiy, V. V., et al. (2011). Regional slow waves and spindles in human sleep. *Neuron* 70, 153-169.

45. Nishida M, Uchida S, Hirai N, Miwakeichi F, Maehara T, Kawai K, et al. (2005). High frequency activities in the human orbitofrontal cortex in sleep-wake cycle. *Neurosci Lett.*, May 6; 379(2):110-5. Epub 2005 Jan. 21.

46. Nobili L, De Gennaro L, Proserpio P, Moroni F, Sarasso S, Pigorini A, De Carli F and Ferrara M. (2012). Local aspects of sleep: observations from intracerebral recordings in humans. *Ferrara. Prog Brain Res.*, 199:219-32. doi: 10.1016/B978-0-444-59427-3.00013-7.

47. Norman R G, Pal I, Stewart C, Walsleben J A, Rapoport D M. (2000). Interobserver agreement among sleep scorers from different centers in a large dataset. *Sleep.*, 23:901-8.

48. Pardey J, Roberts S, Tarassenko L, Stradling J. (1996). A new approach to the analysis of the human sleep/wakefulness continuum. *J Sleep Res.*, 5:201-10.

49. Pahwa M, Kusner M, Hacker C D, Bundy D T, Weinberger K Q, Leuthardt E C. (2015). Optimizing the Detection of Wakeful and Sleep-Like States for Future Electrocorticographic Brain Computer Interface Applications. *PLoS One*, November 12; 10(11):e0142947. doi: 10.1371/journal.pone.0142947. eCollection 2015.

50. Papalambros N A, Santostasi G, Malkani R G, Braun R, Weintraub S, Paller K A, Zee P C. (2017) Acoustic Enhancement of Sleep Slow Oscillations and Concomitant Memory Improvement in Older Adults. *Front Hum Neurosci.* 11:109.

51. Priesemann V, Valderrama M, Wibral M, Le Van Quyen M. (2013). Neuronal avalanches differ from wakefulness to deep sleep—evidence from intracranial depth recordings in humans. *PLoS Comput Biol.*, 9(3):e1002985. doi: 10.1371/journal.pcbi.1002985. Epub 2013 Mar. 21. PMID: 23555220.

52. Plesinger F, Jurco J, Halamek J, Jurak P. (2015). SignalPlant. Brno, Czech Republic: Institute of Scientific Instruments of CAS. Retrieved from https://signalplant.codeplex.com.

53. Quandt F, Reichert C, Hinrichs H, Heinze H, Knight R and Rieger J. (2012). Single trial discrimination of individual finger movements on one hand: a combined MEG and EEG study. *NeuroImage*, 59 3316-24.

54. Ramgopal, Sriram, et al. (2014) "Seizure detection, seizure prediction, and closed-loop warning systems in epilepsy." *Epilepsy & Behavior* 37, 291-307.

55. Rechtschaffen A, Kales A. (1968). A Manual of Standardized Terminology, Techniques and Scoring System for Sleep Stages of Human Subjects. U.S. Government Printing Office; Washington, D.C.

56. Salanova, Vicenta, et al. (2015) "Long-term efficacy and safety of thalamic stimulation for drug-resistant partial epilepsy." *Neurology*, 84(10): 1017-1025.

57. Santostasi G, Malkani R, Riedner B, Bellesi M, Tononi G, Paller K A, Zee P C. (2016) Phase-locked loop for precisely timed acoustic stimulation during sleep. J Neurosci Methods.; 259: 101-14.

58. Schiff S J. (2005). Dangerous phase. *Neuroinformatics*, 3: 315-318.

59. Schulz H. (2008). Rethinking Sleep Analysis. Comment on the AASM Manual for the Scoring of Sleep and Associated Events. *J Clin Sleep Med.*, April 15; 4(2): 99-103. PMCID: PMC2335403.

60. Siclari F, Baird B, Perogamvros L, Bernardi G, LaRocque J J, Riedner B, Boly M, Postle B R, Tononi G (2017) The neural correlates of dreaming. Nat Neurosci 20:872-878.

61. Sixel-Döring, F., Schweitzer, M., Mollenhauer, B. & Trenkwalder, C. Intraindividual variability of REM sleep behavior disorder in Parkinson's disease: a comparative assessment using a new REM sleep behavior disorder severity scale (RBDSS) for clinical routine. J. Clin. Sleep Med. 7, 75-80 (2011)

62. Stead M, Bower M, Brinkmann B H, Lee K, Marsh W R, Meyer F B, et al. (2010) Microseizures and the spatiotemporal scales of human partial epilepsy. Brain. 133:2789-97.

63. Tzourio-Mazoyer N, Landeau B, Papathanassiou D, Crivello F, Etard O, Delcroix N, Joliot M. (2002). Automated anatomical labeling of activations in SPM using a macroscopic anatomical parcellation of the MNI MRI single-subject brain. *NeuroImage*, 15(1), 273-289. doi: 10.1006/nimg.2001.0978.

64. Valderrama M, Crépon B, Botella-Soler V, Martinerie J, Hasboun D, Alvarado-Rojas C, Baulac M, Adam C, Navarro V, Le Van Quyen M. (2012). Human gamma oscillations during slow wave sleep. *PLoS One*, 7(4): e33477. doi: 10.1371/journal.pone.0033477. Epub 2012 Apr. 4. PMID: 22496749.

65. Van Gompel J J, Klassen B T, Worrell G A, Lee K H, Shin C, Zhao C Z, Brown D A, Goerss S J, Kall B A, Stead M (2015) Anterior nuclear deep brain stimulation guided by concordant hippocampal recording.

66. Walter, G. (1936). The location of cerebral tumors by electroencephalography. *Lancet* 2, 305-308.

67. Warren C. P. et al. (2010). Synchrony in Normal and Focal Epileptic Brain: The Seizure Onset Zone Is Functionally Disconnected. *Journal of Neurophysiology*, 104, no. 6 (Oct. 6, 2010): 3530-39. doi:10.1152/jn.00368.2010.

68. Worrell G A, Parish L, Cranstoun S D, Jonas R, Baltuch G, Litt B. (2004). High-frequency oscillations and seizure generation in neocortical epilepsy. *Brain*, 127: 1496-1506.

69. Worrell, G. A., Gardner, A. B., Stead, S. M., Hu, S., et al. (2008). High-frequency oscillations in human temporal lobe: simultaneous microwire and clinical macroelectrode recordings. *Brain*, 131, 928-937.

70. Worrell, G. A., Jerbi, K., Kobayashi, K., Lina, J. M., et al. (2012). Recording and analysis techniques for high-frequency oscillations. *Prog Neurobiol*, 98, 265-278.

71. Zaveri H P, Duckrow R B, Spencer S S. (2000). The effect of a scalp reference signal on coherence measurements of intracranial electroencephalograms. *Clin Neurophysiol*, 111: 1293-1299.
72. Zempel J M, Politte D G, Kelsey M, Verner R, Nolan T S, Babajani-Feremi A, Prior F, Larson-Prior L J. (2012). Characterization of scale-free properties of human electrocorticography in awake and slow wave sleep States. *Front Neurol.*, June 12; 3:76. doi: 10.3389/fneur.2012.00076. eCollection 2012. PMID: 22701446.

What is claimed is:

1. A computerized method of classifying a behavioral state of a brain comprising:
   providing a plurality of sensors configured to detect an electrical activity of the brain;
   providing one or more processors communicably coupled to a user interface and the plurality of sensors;
   receiving a signal from each of the plurality of sensors;
   filtering the signal(s) into a set of frequency bands for each sensor;
   calculating an absolute power and a relative power for each of the frequency bands for each sensor using the one or more processors;
   automatically selecting one or more of the plurality of sensors based on the absolute power and the relative power for each of the frequency bands for each sensor and one or more selection criteria using the one or more processors;
   calculating at least one measured value from the signal(s) of the selected sensor(s) using the one or more processors;
   classifying the behavioral state as: (a) an awake state whenever the measured value(s) for the selected sensor(s) is lower than a first threshold value, (b) a sleep state (N1 or N2) whenever the measured value(s) for the selected sensor(s) is equal to or greater than the first threshold value and the measured value(s) is not greater than a second threshold value, or (c) a slow wave sleep state (N3) whenever the measured value(s) from the selected sensor(s) is greater than the first threshold value and the measured value(s) is greater than the second threshold value; and
   providing a notification of the classified behavioral state to the user interface.

2. The method of claim 1, further comprising automatically mapping one or more spatial and temporal patterns of the signals during the classified behavioral state and one or more transitions between the classified behavioral states.

3. A system for classifying a behavioral state of a brain comprising:
   a sensor interface and/or electrode interface;
   a plurality of sensors;
   a user interface;
   a data storage or memory; and
   one or more processors communicably coupled to the sensor interface and/or electrode interface, the user interface and data storage or memory, wherein the one or more processors:
      receive a signal from each of a plurality of sensors via the sensor interface and/or electrode interface,
      filter the signal(s) into a set of frequency bands for each sensor,
      calculate an absolute power and a relative power for each of the frequency bands for each sensor,
      automatically select one or more of the plurality of sensors based on the absolute power and the relative power for each of the frequency bands for each sensor and one or more selection criteria,
      calculate at least one measured value from the signal(s) of the selected sensor(s),
      classify the behavioral state as: (a) an awake state whenever the measured value(s) for the selected sensor(s) is lower than a first threshold value, (b) a sleep state (N1 or N2) whenever the measured value(s) for the selected sensor(s) is equal to or greater than the first threshold value and the measured value(s) is not greater than a second threshold value, or (c) a slow wave sleep state (N3) whenever the measured value(s) from the selected sensor(s) is greater than the first threshold value and the measured value(s) is greater than the second threshold value, and
      provide a notification of the classified behavioral state to the user interface.

4. The system of claim 3, wherein the plurality of sensors are configured to detect an electrical activity of the brain communicably coupled to the sensor interface and/or electrode interface.

5. The system of claim 3, further comprising one or more remote control or monitoring devices communicably coupled to the user interface.

6. The system of claim 3, wherein the one or more processors further classify the brain behavioral state as a drowsy state (N1), a REM state, a microstate within one of the drowsy state (N1), the sleep state (N2) and the slow wave sleep state (N3), a brain state characterized by abundant or excessive pathological activity, or a brain state otherwise identified as representing an elevated probability for occurrence of a seizure.

7. The system of claim 3, wherein the one or more processors further provide an alert whenever the classified behavioral state is different than a previous classified behavioral state.

8. The system of claim 3, wherein the first threshold value comprises a first Delta power value and the second threshold value comprises a second Delta power value.

9. The system of claim 3, wherein the one or more processors further pre-process the signals by:
   detecting an abnormal amplitude distortion in the signals; or
   detecting a seizure or an abnormal electrophysiological condition using the signals; or
   detecting a high 60 or 50 Hz line interference in the signals.

10. The system of claim 3, wherein the one or more selection criteria comprises:
    a power spectral features extraction; or
    a clustering algorithm comprising a K-means, hierarchical tree, t-SNE, deep learning, neural network, t-SNE, isomap, Sammon mapping, linear embedding, or unsupervised deep embedding clustering algorithm; or
    one or more measures of separability.

11. The system of claim 3, wherein the one or more selection criteria comprising a K-NN clustering algorithm with Euclidean distance measure where inter and intra-cluster distance are used as parameters for selection of only one sensor.

12. The system of claim 3, wherein the one or more processors further select a target brain location for the plurality of sensors from one or more of a cortex, hippocampus, thalamus, brain stem, basal ganglia, subthalamic nucleus, globus pallidus or other movement circuitry structures and muscles via EMG or ENG or actigraphy.

13. The system of claim 3, wherein the set of frequency bands are all within the range of 0.1 Hz to 600 Hz.

14. The system of claim 3, wherein the one or more processors further decimate all frequency bands below 55 Hz prior to filtering the signal(s).

15. The system of claim 3, wherein:
the set of frequency bands comprise 0.1-4 Hz, 4-8 Hz, 8-13 Hz, 13-30 Hz, 0.1-30 Hz, 30-55 Hz, 65-115 Hz, 125-175 Hz, and 185-235 Hz;
the absolute power is calculated using $$P_{Abs}(s, e_s, b, k) = \frac{1}{N}\sum_{1}^{N} V(n)^2 [\mu V^2];$$

the relative power is calculated using and $$P_{Rel}(s, e_s, b, k) = \frac{P_{Abs}(s, e_s, b, k)}{\sum_{b=1}^{8} P_{Abs}(s, e_s, b, k)} [AU];$$

wherein s is a subject number, $e_s$ is one of the sensors, b is one of the frequency bands, k is an epoch of data, N is a number of data points in each epoch, and V(n) is an unipolar voltage at a given discrete time n in μV.

16. The system of claim 3, wherein the plurality of sensors comprise one or more electrodes communicably coupled to the one or more processors via the sensor interface and/or electrode interface, wherein an electrical stimulation is provided to the brain via the one or more electrodes.

17. The system of claim 3, wherein the one or more processors further automatically map one or more spatial and temporal patterns of the signals during the classified behavioral state and one or more transitions between the classified behavioral states.

18. The system of claim 3, wherein the one or more processors select automatic or manual feature selection or sensor selection.

19. The system of claim 3, wherein the one or more processors further use training signal processing and a machine learning system to identify one or more suitable sensor configurations for an automated or semi-automated classification of the behavioral state.

* * * * *